United States Patent [19]
Anderson et al.

[11] Patent Number: 5,431,509
[45] Date of Patent: Jul. 11, 1995

[54] INTERLOCKING MODULE SYSTEM

[75] Inventors: Jerald W. Anderson, Spring Lake Park; Tighe M. Belden; Philip C. Dretzka, both of Minneapolis; Leonard J. Gramse, St. Paul; Gerald L. Oja, Woodbury; Kent R. Struble, Mahtomedi; Daniel M. Sutherland, St. Paul; Mark A. Toycen, Cottage Grove, all of Minn.

[73] Assignee: Minnesota Mining and Manufacturing Company, St. Paul, Minn.

[21] Appl. No.: 260,001

[22] Filed: Jun. 15, 1994

Related U.S. Application Data

[63] Continuation of Ser. No. 976,404, Nov. 13, 1992, abandoned, which is a continuation-in-part of Ser. No. 797,691, Nov. 25, 1991, abandoned.

[51] Int. Cl.$^6$ .............................................. F16B 2/02
[52] U.S. Cl. ................................... 403/381; 403/24; 403/322; 403/331; 403/380; 248/225.1
[58] Field of Search .......... 403/381, 380, 24, 321–322, 403/345, 330–331, 339–341, 325, 327, 376, 398, 399, 409.1; 604/65–67, 80, 150–155; 248/225.1, 223.4, 224.1, 224.2, 222.1; 211/107

[56] References Cited

U.S. PATENT DOCUMENTS

| | | | |
|---|---|---|---|
| D. 278,181 | 3/1985 | Archibald et al. | D24/8 |
| D. 287,055 | 12/1986 | Fick et al. | D24/29 |
| 2,243,517 | 5/1941 | Adamson | 211/176 |
| 3,669,392 | 6/1972 | Saunders | 248/121 |
| 3,790,116 | 2/1974 | Schulman | 248/124 |
| 3,985,133 | 10/1976 | Jenkins et al. | 128/214 F |
| 4,202,333 | 5/1980 | Thill et al. | 128/218 A |
| 4,236,880 | 12/1980 | Archibald | 417/478 |
| 4,277,226 | 7/1981 | Archibald | 417/38 |
| 4,298,000 | 11/1981 | Thill et al. | 128/218 A |
| 4,322,201 | 3/1982 | Archibald | 417/279 |
| 4,356,475 | 10/1982 | Neumann et al. | 340/521 |
| 4,371,285 | 2/1983 | Behar | 403/339 |

(List continued on next page.)

FOREIGN PATENT DOCUMENTS

| | | |
|---|---|---|
| 2215331 | 10/1973 | Germany . |
| 3842051 | 12/1989 | Germany . |
| 9000646 | 8/1990 | Germany . |
| WO93/21978 | 11/1993 | WIPO . |

OTHER PUBLICATIONS

Numerous brochures enclosed in a folder titled "AVI Infusion Therapy Systems" including: 3M IV Poles: 3M Delivers Space-saving solutions; AVI 200A Infusion Pump; AVI 400A Infusion Pump; AVI480 and 480CM Infusion Pump; AVI Micro 210A Infusion Pump; AVI 285 and 285CM Micro Infusion Pump; AVI 840 Dual Channel Infusion Pump; and AVI Micro 845 Dual Channel Infusion Pump; AVI 600 Syringe Pump; The 3M IV Flow Regulator; AVI Administration Sets: Infusion Pump Sets; Medifuse: Setting the Standard for Homecare Patient IV Delivery Systems; and When it all depends on you, depends on us. AVI Nurse Clinican Services. All dated between 1988–1991.

Imed Corporation brochure "Gemini TM Administration Sets".

*Primary Examiner*—Randolph A. Reese
*Assistant Examiner*—Harry C. Kim
*Attorney, Agent, or Firm*—Gary L. Griswold; Walter N. Kirn; Stephen W. Bauer

[57] ABSTRACT

A system for interlocking a plurality of modules, such as medical instrument modules (e.g., infusion pumps), in side-by-side relationship such that not more than one module can be mounted on each side of a center module. The modules are interchangeable in that any module of the system can be a center module or a side module. In the preferred embodiment, latching arms on a module are automatically moved as the module is mounted on a pole stand to allow other "side" modules to be mounted on that "center" module. The latching arms of the "side" modules prevent additional modules from being mounted on the side modules. Other embodiments are described as well.

85 Claims, 10 Drawing Sheets

U.S. PATENT DOCUMENTS

| | | | |
|---|---|---|---|
| 4,430,079 | 2/1984 | Thill et al. | 604/154 |
| 4,535,870 | 8/1985 | Lindsay | 181/141 |
| 4,564,732 | 1/1986 | Lancaster et al. | 200/307 |
| 4,597,754 | 7/1986 | Thill et al. | 604/154 |
| 4,637,749 | 1/1987 | Jones et al. | 403/322 |
| 4,648,737 | 3/1987 | Lake, Jr. et al. | 403/322 |
| 4,702,448 | 10/1987 | LoJacono et al. | 248/231.7 |
| 4,756,706 | 7/1988 | Kerns et al. | 604/66 |
| 4,844,397 | 7/1989 | Skakoon et al. | 248/231.7 |
| 4,867,404 | 9/1989 | Harrington et al. | 248/231.4 |
| 4,867,598 | 9/1989 | Winter, IV | 403/381 |
| 4,898,578 | 2/1990 | Rubalcaba, Jr. | 604/66 |
| 4,905,944 | 3/1990 | Jost et al. | 248/125 |
| 4,970,900 | 11/1990 | Shepherd et al. | 73/756 |
| 5,017,192 | 5/1991 | Dodge et al. | 604/250 |
| 5,022,538 | 6/1991 | Richmond et al. | 211/113 |
| 5,207,642 | 5/1993 | Orkin et al. | 604/65 |
| 5,242,407 | 9/1993 | Struble et al. | 604/151 |

INTERLOCKING MODULE SYSTEM

This application is a continuation application of U.S. patent application Ser. No. 07/976,404, filed Nov. 13, 1992, which is a continuation-in-part application of U.S. patent application Ser. No. 07/797,691, filed Nov. 25, 1991, both now abandoned.

BACKGROUND OF THE INVENTION

The invention relates generally to a system for mounting modules on one another, and more particularly to a system for mounting modules, such as medical instrument modules, on a pole stand.

In modern medical practice a variety of diagnostic and therapeutic instruments are used, sometimes to such a degree that floor and shelf space near the patient's bedside is at a premium. One known solution to the problem of mounting instrument modules is the use of a pole stand, which allows equipment to be mounted vertically over a relatively small footprint on the floor. Often such pole stands have wheels for the convenience of the operator in moving them to where they are needed. It is a well known problem in the hospital setting that such wheeled stands are easily unbalanced upon, for example, crossing thresholds or exiting elevators.

A related concern is matter of rapidly mounting and demounting various instruments in a hospital setting. In a crisis situation, it can be important that the proper mounting of an instrument module be accomplished expeditiously. Even in routine operations, a convenient and reliable mounting system would increase efficiency while enhancing patient comfort. In particular, infusion therapy is performed on many patients in the hospital, and due to incompatibilities in drug chemistry or infusion regimen, this often requires several infusion lines. Over the course of a hospital stay, the number of infusion lines, and hence the number of infusion pumps managing the flow within them, is likely to vary. The cost of patient care is reduced if the infusion pumps can rapidly be redeployed where needed.

Examples of infusion pumps that have typically been mounted on pole stands are shown in co-assigned U.S. Pat. No. 5,017,192 and U.S. Pat. No. Des. 278,181. Typically, a single infusion pump has been mounted on the pole stand at one vertical location along the stand. If additional infusion pumps were needed, they would be mounted on separate pole stands, or at a different vertical location along the same pole stand, or on specially designed multi-pole adaptors or stands that provide a plurality of spaced apart vertical pole sections for mounting infusion pumps. Such infusion pumps have been available from Minnesota Mining and Manufacturing Company, St. Paul, Minn., under various trade designations, such as the "AVI 200", "AVI 400" and "AVI 480" model series.

Dual channel infusion pumps have also been available in which one pump housing contains two separately controllable infusion pumps. Dual channel infusion pumps have been available from Minnesota Mining and Manufacturing Company, St. Paul, Minn., under the trade designations "AVI 840" and "AVI MICRO 845". In the case of dual channel infusion pumps, space on the pole stands is economized by mounting one housing on the pole stand to provide two pumps and two flow channels. Another dual channel infusion pump is available from IMED Corporation, San Diego, Calif., under the trade designation "GEMINI PC2". Of course, one disadvantage of any dual channel infusion pump is that in effect two infusion pumps are provided even in situations where only one pump is needed.

Specially designed pole stands have been used to support a plurality of infusion pumps. One such pole stand has been sold by Minnesota Mining and Manufacturing Company, St. Paul, Minn., under the trade designation "Model 166 Multipump IV Pole". The "Model 166" pole stand has a lower single pole section supporting an upper multiple pole section, which comprises a plurality of spaced apart pole sections. The upper pole sections of that pole stand have been used to support more than one infusion pump at the same vertical level. Specially designed adaptors have also been available to provide more than one spaced apart vertical pole section on a single pole stand. An adaptor of that type has been available from Minnesota Mining and Manufacturing Company under the trade designation "Model 146 IV Pole Adaptor".

U.S. Pat. Nos. 4,756,706 and 4,898,578 show a drug infusion system with calculator. That system includes a plurality of infusion pump modules arranged in a vertical stack along with a central management unit, all of which are supported on a single pole stand. The modules are electronically interlinked with the central management unit. U.S. Pat. No. 4,356,475 (Neumann et al.) shows a system containing a predetermined number of monitoring devices and at least one central station. That system includes equipment having a bay into which slide-in modules can be introduced in levels one above the other.

SUMMARY OF THE INVENTION

The invention provides a system of interconnecting modules, such as medical device modules (e.g., an infusion pump), such that one module (designated the "center" module) can have two modules (designated the "side" modules) connected on opposite sides of the center module but that prevents additional modules from being mounted on the side modules. The modules of the invention are designed to be interchangeable in so far as the system is concerned, i.e., a "side" module of one set-up can be used as a "center" module of another set-up and visa versa. The invention also provides such a system in which the act of attaching the "center" module to a pole stand automatically allows the attachment of "side" modules to the "center" module, which the "center" module would prevent absent its attachment to the pole stand.

Generally, a system of the invention is adapted for interlocking a plurality interchangeable modules in side-by-side relationship. The modules of the invention each generally comprises a frame having opposite sides, and interlocking means on the frame adapted for attaching at least two other modules of the system to the module. The interlocking means includes condition-setting means for setting the interlocking means in a first condition for mounting the module on another module of the system or a second condition for mounting other module(s) of the system thereon. The arrangement is such that (a) when the interlocking means is set in its first condition the interlocking means is capable of being mounted on the interlocking means of another module of the system that has been set in its second condition but the interlocking means of the module is not capable of having mounted thereon the interlocking means of another module of the system, and (b) when the interlocking means is set in its second condition it is capable of having mounted thereon the interlocking means of two other modules of the system that have been set in their first condition.

Preferably, each module includes securing means for securing the module to a pole, and automatic means for setting the module in its second condition upon securing the module to a pole via the securing means.

The interlocking means of each module may conveniently comprise one of each a male and a female dovetail-type slide connection on opposite sides of the module. The male dovetail-type slide connection is complementary to the female dovetail-type slide connection of other modules of the system. The male and female dovetail-type slide connections are arranged along each module such that the direction of slide in the connection is generally along a vertical axis.

Also, conveniently, the condition-setting means of each module may include a shoulder adjacent each of the male and female dovetail-type slide connections, and shoulder-engaging means, such as a latching arm, for engaging a shoulder on another module of the system. The shoulder-engaging means enable the module to be mounted on the other module when the condition-setting means of the module is in its first condition and one of the male or female dovetail-type slide connections of the module is interconnected with the other of the male or female dovetail-type slide connections of the other module. The shoulder-engaging means is movable, as the interlocking means is converted to its first condition from its second condition, to a position in which it cannot engage the shoulder of an adjacent module when one of the male or female dovetail-type slide connections of the module is interconnected with the other of the male or female dovetail-type slide connections of the adjacent module.

In one alternative aspect of the invention, the interlocking means of each module comprises a pair of generally L-shaped support bodies rotatably mounted on opposite sides of the module. Each of the support bodies has two legs including one leg comprising a male dovetail-type slide connection adapted for connection with a complementary female dovetail-type slide connection of another module, and another leg comprising a female dovetail-type slide connection adapted for connection with a complementary male dovetail-type slide connection of another module. In this alternative, the condition-setting means comprises means for pivotably mounting the support bodies on opposite sides of the module, with the male dovetail-type slide connections of the module being aligned in one direction and the female dovetail-type slide connections of the module being aligned in another direction generally perpendicular to the direction of the male dovetail-type slide connections. The support bodies are pivotable between a first position, wherein one aligned pair of the male or female dovetail-type slide connections are aligned in the vertical direction, and a second position, wherein the other aligned pair of the male or female dovetail-type slide connections are aligned in the vertical direction.

In one preferred aspect of the invention, the module is in the form of a medical instrument module, such as an infusion pump, that is adapted for use in an interlocking system of similar medical instrument modules that are adapted to be mounted in side-by-side relationship on a pole stand. The module generally comprises a frame having opposite sides, securing means for securing the module to a pole, and at least two slide connections mounted on opposite sides of the module. The slide connection on one side of the module is complementary to the slide connection on the other side of the module, and the slide connections are arranged along the module such that the direction of slide in the connection is generally along a vertical axis when the module is in use. At least two latching surfaces are provided on the module, each corresponding to one of the slide connections. The latching surfaces are adapted for engaging a latching arm of a similar module when the slide connection of the module is interconnected with a complimentary slide connection of the similar module. A latching arm is movably mounted in the frame, and is adapted for engaging a latching surface on a similar module to enable the module to be mounted on the similar module. More specifically, the latching arm is movable between a first position and a second position. In the first position, the latching arm extends relative to the latching surfaces and slide connections a distance sufficient to engage the shoulder of a similar module when one of the slide connections are mounted on the slide connection of the similar module and wherein the latching arm blocks the slide connection from having a slide connection of a similar module mounted thereon. In the second position, the latching arm is withdrawn relative to said latching surfaces and slide connections to allow a slide connection of a similar module to be mounted on said slide connection.

Preferably, at least two latching arms are provided at opposite sides of said module, with each latching arm corresponding to one of said slide connections. Each arm includes a rack portion having gear teeth. The module also includes a gear rotatably mounted on the frame, with the gear teeth of the gear in intermeshing relationship with the gear teeth of the arms such that rotation of the gear in one direction withdraws the arms from the first position to their second position. Biasing means, such a spring, may also be provided for biasing said arms toward their first position. A tongue on one of the arms extends into the securing means such that when the tongue is engaged by a pole to which the securing means is secured, the tongue is moved by the pole to move the arms to their second position.

Conveniently, the slide connections comprise male and female dovetail-type slide connections on opposite sides of the module, with the male and female dovetail-type slide connections being complementary to one another. The dovetail-type slide connections have upper and lower ends relative to the intended use of the module. The latching surfaces are provided on shoulders on opposite sides of the module adjacent the upper ends of the slide connections. Each shoulder includes a flange extending generally vertically upwardly from the shoulder along an outer edge of the shoulder and to define at least a portion of the latching surface. Each latching arm preferably has a notch therein generally adjacent an outer end of the latching arm. The notches of the latching arms are adapted to receive the flanges of similar modules when the latching arms are in their first position.

In another preferred aspect of this invention, a medical device module is adapted for use in an interlocking system of similar medical device modules that are adapted to be mounted in side-by-side relationship on a pole stand. The module comprises securing means for securing the module to a pole, and at least two slide connections mounted on opposite sides of said module, with the slide connection on one side of the module being complementary to the slide connection on the other side of the module. Two pair of opposed latching shoulders are provided on the same opposite sides of the module as the two slide connections, with each pair of opposed latching shoulders corresponding to one of the slide connections. Two latching arms are provided. Each latching arm is movably mounted in the module for engaging a pair of opposed latching shoulders on a similar module to enable the module to be mounted on the similar module. The latching arms are movable between an extended position and a withdrawn position. In the extended position, the latching arms extend relative to the slide connections a distance sufficient to be received between a pair of opposed latching shoulders of a similar module when one of the slide connections are mounted on the slide connection of the similar module, and the latching arms block the slide connections from having a slide connection of a similar module mounted thereon. In the withdrawn position, the latching arms are withdrawn relative to the slide connections to allow a slide connection of a similar module to be mounted on the slide connections. Manually operable means is provided for moving the latching arms from their extended position toward their withdrawn position to permit moving one of the latching arms past the opposed latching shoulders of a similar module on which the module is mounted to permit dismounting the module from the similar module.

A second aspect of the invention is a system comprising at least two medical device modules as described above.

Preferably, the manually operable means comprises a push button mounted on each latching arm to facilitate manually pushing the latching arms from their extended position toward their withdrawn positions.

Also, preferably, one of the latching shoulders of each pair of opposed latching shoulders is formed on a structure having a sloped surface along the side facing away from the other latching shoulder. The sloped surface urges the latching arm of a similar module toward its withdrawn position when the slide connection of the similar module is being slidably mounted on the slide connection of the module, until the latching arm of the similar module is received between the pair of opposed latching shoulders. For example, the slide connections may have a direction of slide in the vertical direction, and the sloped surface of the upper shoulder faces generally upwardly. Biasing means is also provided for biasing the latching arms toward their extended position.

Most preferably, automatic means is provided for moving the latching arms against the biasing force of the biasing means to the withdrawn position upon securing the module to a pole via said securing means. Conveniently, each latching arm includes a rack portion having gear teeth. A gear rotatably is mounted in the module, with the gear teeth of the gear in intermeshing relationship with the gear teeth of the rack portions of the latching arms such that rotation of the gear in one direction withdraws the latching arms from their extended position to their withdrawn position. A tongue is provided on one of the latching arms extending into the securing means such that when the tongue is engaged by a pole to which the securing means is secured, the tongue is moved by the pole to move the latching arms to their withdrawn position.

Also, preferably, the slide connections comprise male and female dovetail-type slide connections on opposite sides of the module, with the male and female dovetail-type slide connections being complementary to one another. The dovetail-type slide connections have upper and lower ends relative to the intended use of the module. Each pair of opposed latching shoulders includes an upper latching shoulder and a lower latching shoulder. The lower latching shoulder includes a flange extending generally vertically upwardly from the lower shoulder along an outer edge of the shoulder. The shoulders are generally adjacent the upper ends of the dovetail-type slide connections. Each latching arm has a downwardly-facing notch therein generally adjacent an outer end of the latching arm. The notches of the latching arms are adapted to receive the flanges of similar modules when the latching arms are in their extended position.

Other features will be in part apparent and in part pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
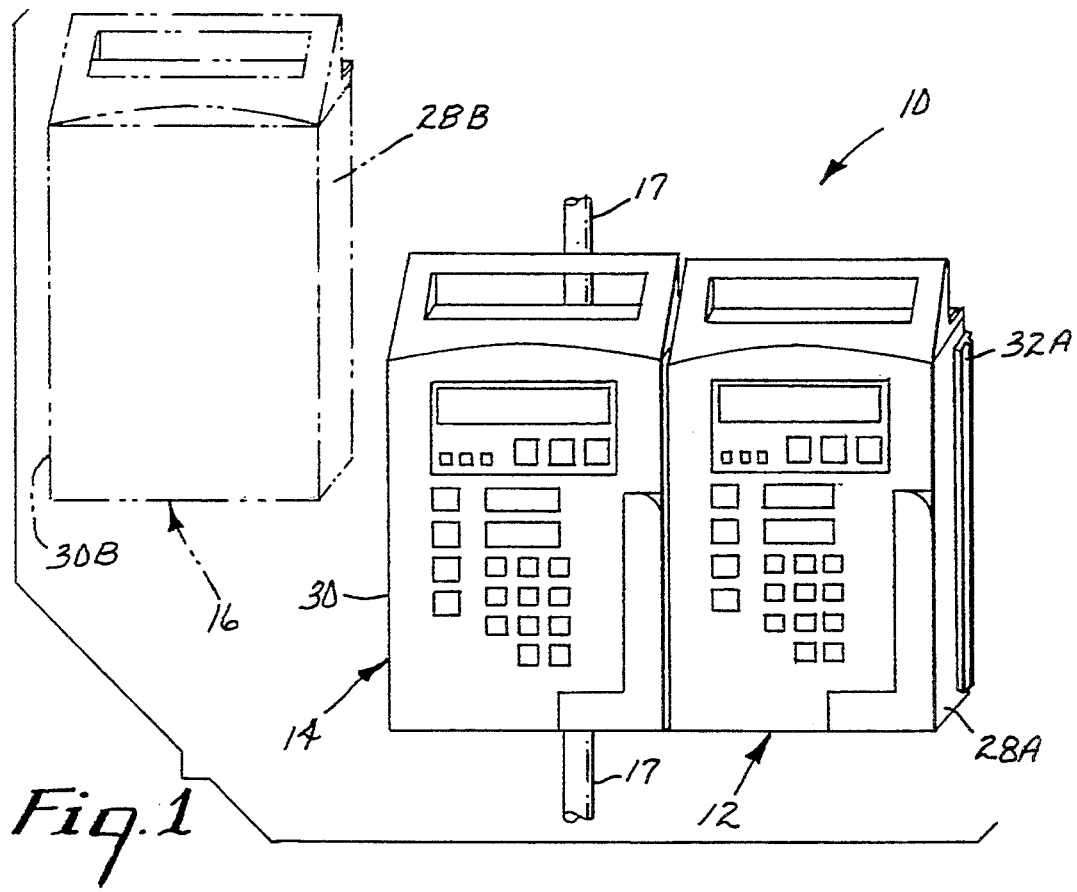
FIG 1 is a frontal perspective view of three modules of the invention illustrating their being mounted on a single pole stand.

As illustrated in FIG. 1, the system 10 of the invention comprises a plurality of interchangeable modules 12, 14 and 16 which are adapted to be releasably interlocked in a side-by-side arrangement supported by one of the modules 14 on a pole stand 17.

The modules 12, 14 and 16 may be in the form of three infusion pumps 12, 14 and 16 of the general type described in U.S. Pat. Nos. 4,236,880; 4,277,226 4,322,201; 5,017,192 and 5,242,407, as well as U.S. patent application Ser. No. 08/070,497, filed Jun. 1, 1993 by Thill, Toycen, Struble and Curran, (all of which are incorporated herein by reference). One or more of the modules 12, 14 and 16 may also be of the general type sometimes referred to as "syringe pumps", such as described in U.S. Pat. Nos. 4,202,333; 4,298,000; 4,430,079 and 4,597,754 (incorporated herein by reference). It is also contemplated that the modules 12, 14 and/or 16 of the invention might include other types of modules, such as other medical instrument modules. Examples include patient monitoring equipment, as well as other types of modules that may be employed in medical procedures.

As used herein, the term "interchangeable" refers to the feature of the modules 12, 14 and 16 being capable of being arranged in each other's position. For example, either one of the "side" modules 12 and 16 in FIGS. 1 and 2 could be repositioned in the center or exchanged with each other, and the "center" pump 14 could be positioned at either side. "Interchangeable" is not intended to refer the function of the modules 12, 14 and 16, e.g., one module could be an infusion pump, and another module of the same system could be a patient monitor.

The modules 12, 14 and 16 illustrated in the drawings are substantially identical, and will first be described with reference to the center module 14 and right side module 12. Corresponding features in the "right side" module 12 and "left side" module 16 are indicated by the same reference numerals as the "center" module 14 but are followed by an "A" or "B" respectively. Regardless of which module 12, 14 or 16 is being described, the relevant features of the other modules of the preferred embodiment are identical.

Module 14 generally comprises a frame 18, and interlocking means on the frame 18 for attaching at least two similar modules (e.g., 12 and 16) having interlocking means to the module 14. The interlocking means includes condition-setting means (e.g., latching arms 20 and 22) for setting the interlocking means in a first condition (FIG. 3) or a second condition (FIG. 4). As illustrated with "right" and "left" modules 12 and 16 in FIGS. 1–3, in the first condition, the interlocking means is adapted for mounting the module 12 or 16 on a similar module 14. For example, the latching arms 20A and 22A of module 12 are shown in their extended position in FIG. 3, and one of the latching arms 20B of module 16 is shown in its extended position in FIG. 4. As illustrated with "center" module 14 in FIGS. 1–2 and 4, in the second condition, the interlocking means is adapted for mounting similar module(s) (e.g., 12 and 14) thereon. For example, the latching arms 20 and 20A of the center module 14 are shown in their retracted position in FIG. 4.

The arrangement is such that, when the interlocking means of a module (e.g., 12) is set in its first condition, the interlocking means is capable of being mounted on the interlocking means of a similar module (e.g., 14) that has been set in its second condition, but the interlocking means of the module 12 is not capable of having mounted thereon the interlocking means of a similar module (e.g., 16) that has been set in its first condition. The arrangement is also such that, when the interlocking means of a module (e.g., 14) is set in its second condition, it is capable of having mounted thereon the interlocking means of at least two similar modules (e.g., 12 and 14) that have been set in their first condition. Various alternatives as to how this can be accomplished will be described below.

For purposes of illustration, the arrangement in the first condition will be described mostly with respect to "right" module 12, and the arrangement in the second condition will be described mostly with respect to "center" module 14. In the preferred embodiment illustrated in FIGS. 1–8, the difference between the first and second conditions is whether the latching arms 20 and 22 are extended as illustrated at 20A and 22A in FIG. 3 or retracted as illustrated at 20 and 22 in FIG. 4.

Figure 3:
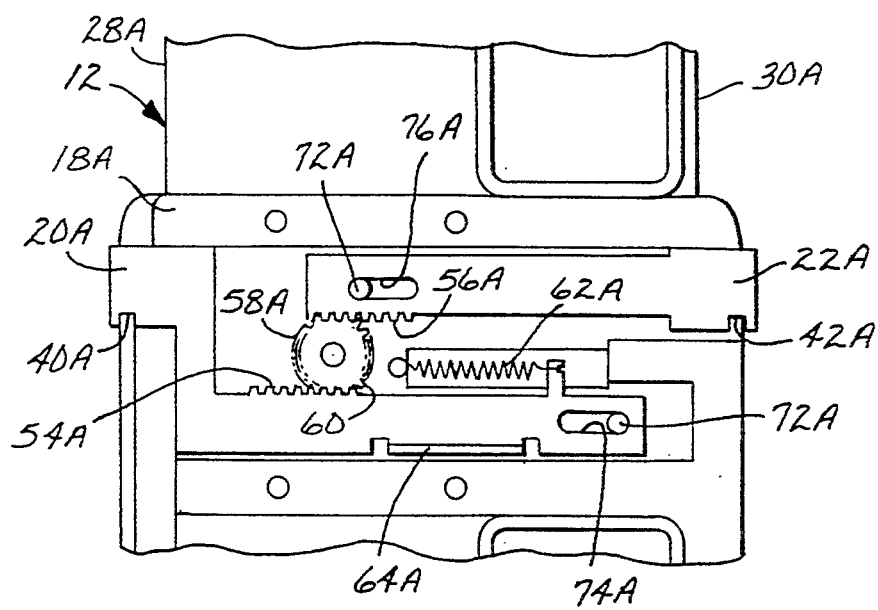
FIG. 3 is a partial cross-sectional view substantially along line 3—3 of FIG. 2 illustrating a first condition of the module in which the module is adapted to be mounted on the side of another module.
Figure 4:
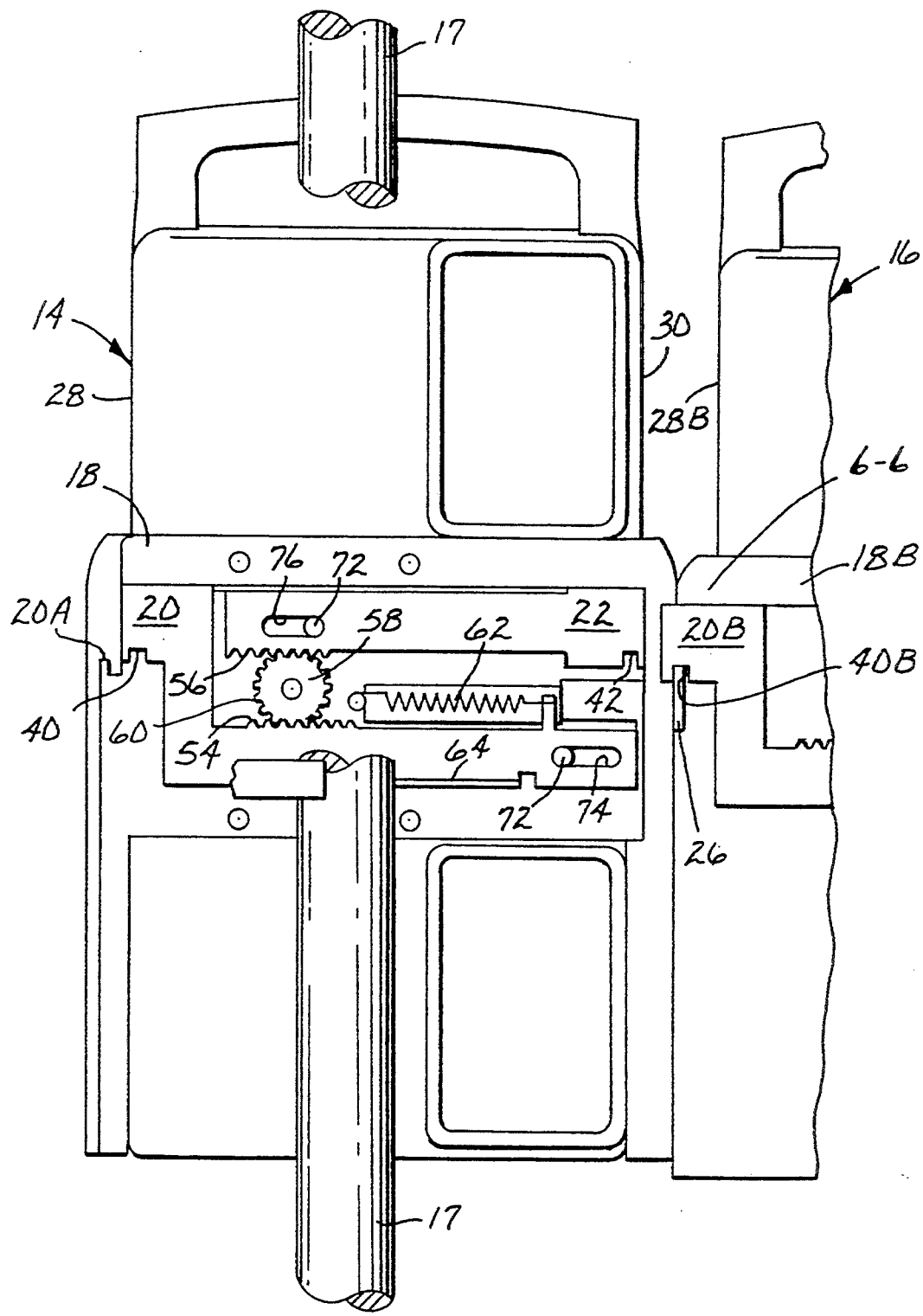
FIG. 4 is a modified cross-sectional view similar to FIG. 3 illustrating a second condition of the module in which the module is adapted to have other modules set in their first condition mounted on its opposite sides.

In the first condition, as shown in FIG. 3, the latching arms 20A and 22A of module 12 are extended to a first position, or as shown in FIG. 4 the latching arms 20B of module 16 are extended to the first position, and with either module 12 or 16 the intended result being to latch onto a corresponding latching surface 24 or 26 of the center module 14 (with corresponding latching arms 20A and 22B) to mount module 12 and 16 on the right or left side 28 or 30 of module 14. In the second condition, the latching arms 20 and 22 of module 14 are retracted to a second position (FIG. 4).

Preferably, at least two slide connections 32 and 34 are provided on opposite sides 28 and 30 of the module 14. The slide connection 32 on one side 28 of each module 14 is complementary to the slide connection 34 on the other side 30 of the module 14. The arrangement is such that the slide connection 32, 32A or 32B on the right side 28 of any module 12, 14 or 16 of one compatible system 10 is complementary to the slide connection 34, 34A or 34B on the left side 30 of any other module 12, 14 or 16 of the same system 10.

Figure 2:
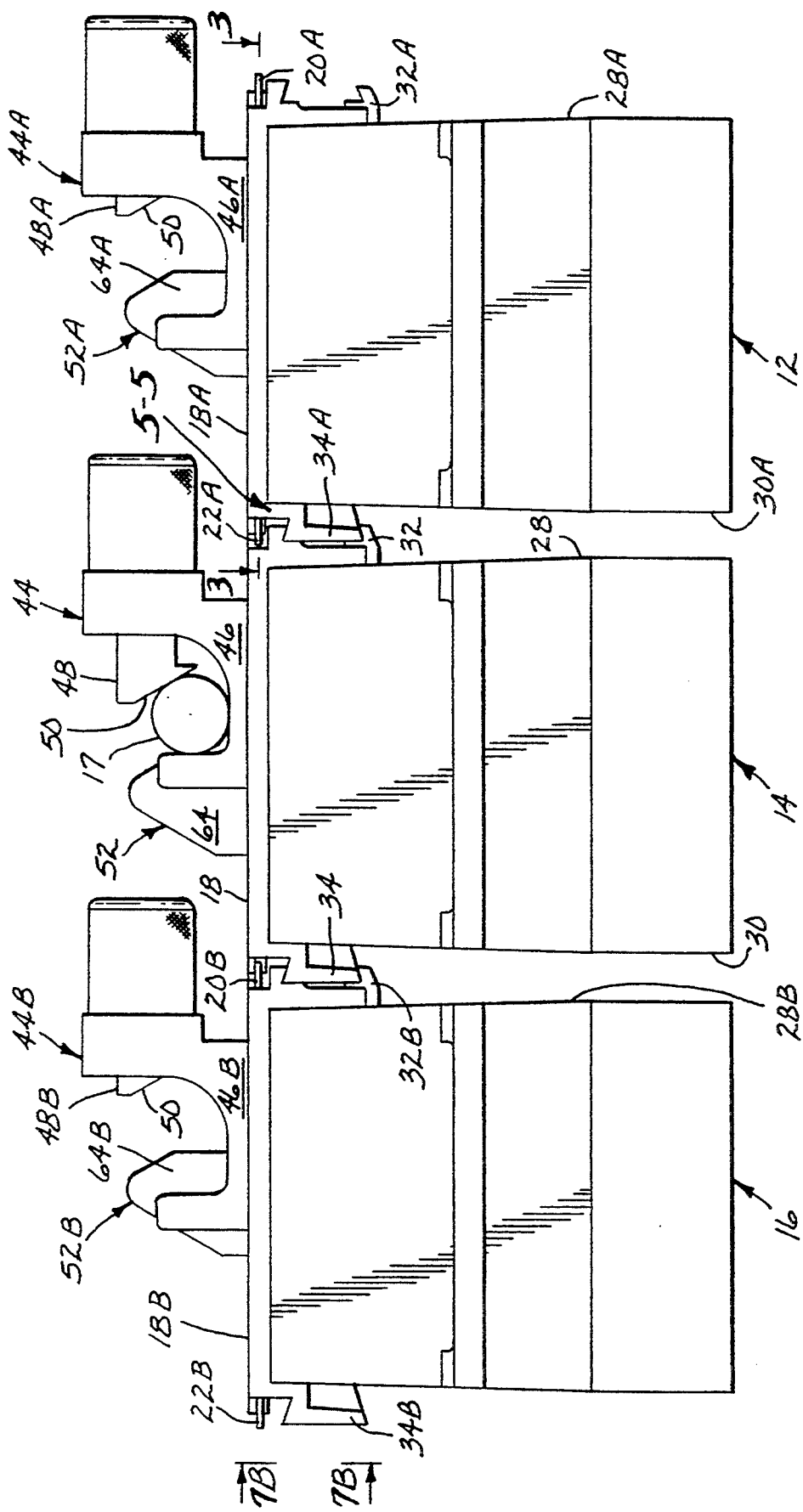
FIG. 2 is a top plan view of the three modules of FIG. 1 mounted on the single pole stand.
Figure 5:
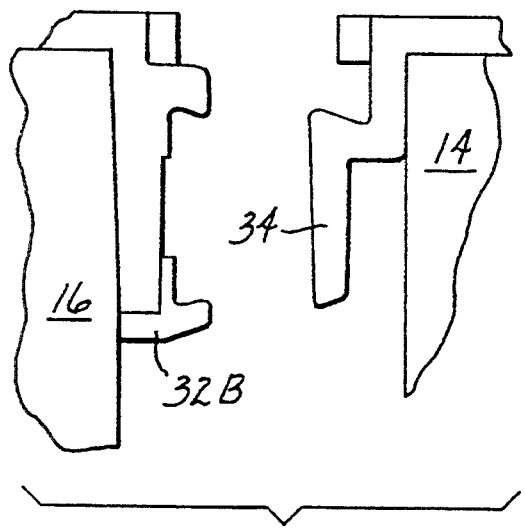
FIG. 5 is an enlarged exploded diagrammatic top view of complementary slide connections on the modules taken at area 5—5 of FIG. 2 illustrating details of slide connections that are adapted to help interlock adjacent modules together.

As used herein, the term "complementary" refers to the feature of the slide connections on opposite sides 28 and 30 of the modules being compatible with one another so as to properly fit each other to interchangeably mount the modules 12, 14 and 16 on one another. For example, as illustrated in FIGS. 2 and 5, the slide connections 32, 32A and 32B on the right sides 28, 28A and 28B of the modules 14, 12 and 16, respectively, may comprise female dovetail-type slide connections 32, 32A and 32B, and the slide connections 34, 34A and 34B on the left sides 30, 30A and 30B may comprise "complementary" male dovetail-type slide connections 34, 34A and 34B. The male dovetail-type slide connections 34, 34A and 34B are adapted to be securely engaged in any of the female dovetail-type slide connections 32, 32A and 32B. FIG. 5 is a diagrammatic top view of area 5—5 in FIG. 2 illustrating that the male dovetail-type slide connections 34A are sized to be closely received in the open area of the female dovetail-type slide connections 32.

As illustrated in FIGS. 1, 2 and 7A–B, the slide connections, e.g., 32A, are arranged along the modules 12, 14 and 16 such that the direction of slide in the connection 32, 32A, 32B, 34, 34A and 34B is generally along a vertical axis when the modules 12, 14 and 16 are in use. This orientation of the slide connections 32, 32A, 32B, 34, 34A and 34B facilitates mounting the side modules 12 and 16 on the center module 14. The side modules 12 and 16 merely have to be raised relative to the center module 14, and the lower end of the appropriate slide connection 34A and 32B of the side modules 12 and 16 slide into or around the complementary slide connection 32 and 34, respectively, of the center module 14 to mount the side modules 12 and 16 on the center module 14.

Figure 7B:
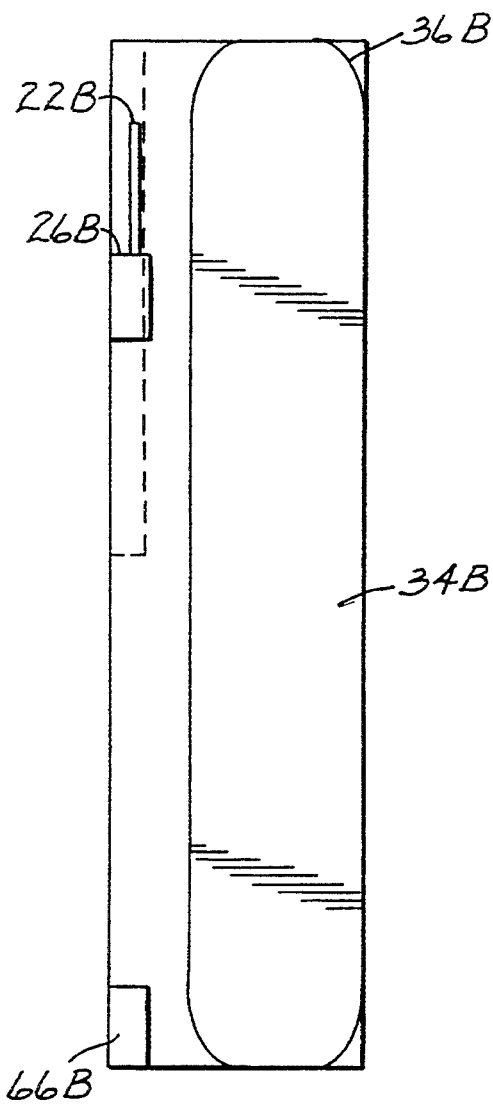
FIG. 7A and 7B are side views of a portion of outer sides the two side modules shown as illustrated in FIG. 2.

In order to facilitate mounting one module on another, the upper and/or lower ends of the male dovetail-type slide connections 34, 34A and 34B are preferably tapered as illustrated at 36B in FIG. 7B to ease their introduction into the open slot area of the female-type slide connections 32, 32A and 32B. The open slot area of the female dovetail-type slide connections 32, 32A and 32B may also be flared outwardly adjacent their upper and/or lower ends as illustrated at 37A in FIG. 7A to guide the male dovetail-type slide connections 34, 34A and 34B into the open slot area of the female slide connections 32, 32A and 32B.

The slide connections 32, 32A, 32B, 34, 34A and 34B preferably extend along a substantial portion of the entire height of the sides 28, 28A, 28B, 30, 30A or 30B of the modules 12, 14 and 16. The height of the slide connections 32, 32A, 32B, 34, 34A and 34B is most preferably at least half of the height of the module 12, 14 or 16. For example, the height of the slide connections 32, 32A, 32B, 34, 34A and 34B may be approximately two thirds of the height of the modules 12, 14 and 16. One example is slide connections 32, 32A, 32B, 34, 34A and 34B having a six inch (150 mm) height on modules 12, 14 and 16 having a nine inch (230 mm) height.

Figure 6:
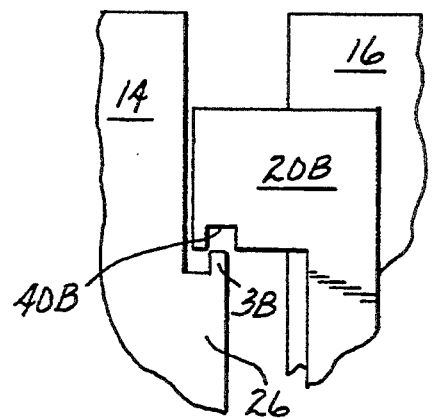
FIG. 6 is an enlarged diagrammatic view of a portion 6—6 of two interlocked modules of FIG. 4 illustrating details of the arrangement when one module is mounted on another.

Preferably, each latching surface (e.g., 26 in FIG. 6) is formed by a shoulder (also 26) including a flange 38 adapted for engaging a latching arm 20B of a module 16 being mounted thereon. The flange 38 extends generally vertically upwardly from the shoulder 26 along an outer edge of the shoulder 26. As illustrated in FIG. 6, a notch 40B is provided in each latching arm 20B generally adjacent the outer end of the latching arm 20B. The notches 40B of the latching arms 20B are adapted to receive the corresponding flanges 38 of a center module 14 when the latching arms 20B and 22B are in their first position. (The notch in the opposite latching arm 22 and 22A is designated by the reference numeral 42 or 42A in FIGS. 3 and 4.)

Figure 7A:
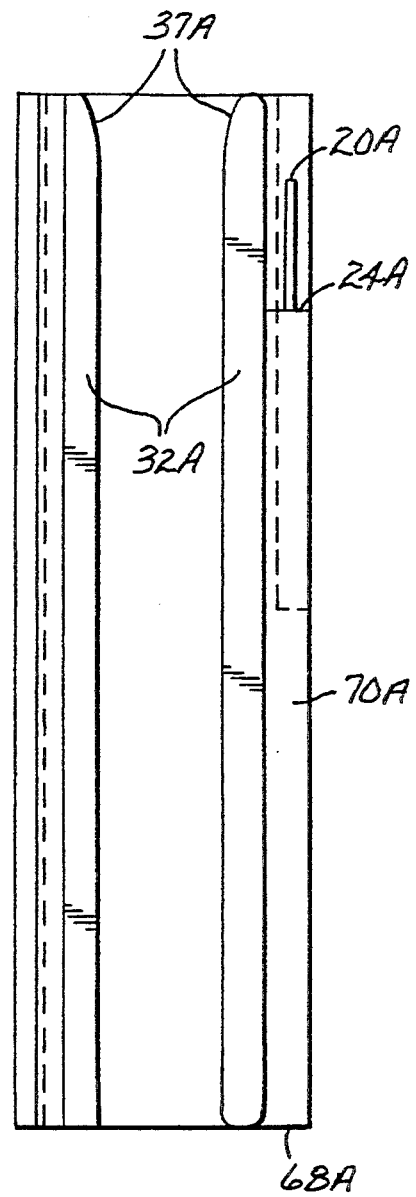

As illustrated in FIGS. 7A and 7B, the shoulders 24 and 26 are generally adjacent the upper ends of the slide connections 32, 32A, 32B, 34, 34A, and 34B. The shoulders 24 and 26 are formed in a generally upwardly-facing direction to support the latching arms 20A or 22A of adjacent modules 12 to mount the adjacent module 12 on the "center" module 14. Alternatively, it is contemplated that the shoulders and latching surfaces (not shown) could be provided adjacent the lower ends of the slide connections.

Each module 12, 14 and 16 has a securing means generally designated 44 (FIG. 2) for securing the module 12, 14 or 16 to the pole 17. As illustrated in FIG. 2, the securing means 44 preferably comprises a generally U or J-shaped clamp bracket 46 forming a generally U or J-shaped opening for receiving the pole 17, and a movable clamp jaw member 48 mounted on one side of the bracket 46 for movement to clamp or release a pole 17 between the jaw member 48 and the opposite side of the bracket 46.

The end surface 50 of the jaw member 48 is most preferably inclined at an angle (e.g., 55–60 degrees) relative to the longitudinal axis of movement AX-2 of the jaw member 48 to apply a clamping force to the pole 17 inwardly relative to the J or U-shaped open area defined by the clamp bracket 46. The end surface 50 of the jaw member 48 may be provided with a suitable texture (e.g., a knurled or ribbed surface or rubber coating) to help secure the module 14 on the pole 17. The securing means may alternatively be of the general type shown in U.S. Pat. No. Des. 278,181 (incorporated herein by reference).

Automatic means 52 is preferably provided for moving the latching arms 20 and 22 to their second position (FIG. 4) upon securing the module 14 to a pole 17 via the securing means 44. Most preferably, each latching arm 20 and 22 includes a rack portion 54 and 56 having gear teeth (also at 54 and 56). A gear 58 is rotatably mounted on the frame 18, with the gear teeth 60 of the gear 58 in intermeshing relationship with the gear teeth 54 and 56 of the latching arms 20 and 22. The arrangement is such that rotation of the gear 58 in one direction (counterclockwise in the drawing) withdraws the latching arms 20 and 22 from the first position (FIG. 4 and latching arm 20A in FIG. 5) to their second position (latching arms 20 and 22 in FIG. 5).

Biasing means (e.g., coil spring 62 or 62A) is provided for biasing the latching arms 20 and 22 or 20A and 22A toward their first position (FIG. 4). The biasing spring 62 or 62A preferably engages the frame 18 at one end of the spring 62 or 62A and one of the latching arms 20 or 20A to bias the latching arms 20, 20A, 20B, 22, 22A and 22B laterally outwardly relative to the module 12, 14 or 16 to their first position.

A tongue 64, 64A is provided on one of the latching arms (left latching arms 20 and 20A in the drawing). As shown in FIG. 2, the tongue 64, 64A or 64B extends into the securing means 44, 44A and 44B such that when the tongue 64 is engaged by a pole 17 to which the securing means 44 is secured, the tongue 64 is moved by the pole 17 to automatically move the latching arms 20 and 22 to their second position.

Figure 8:
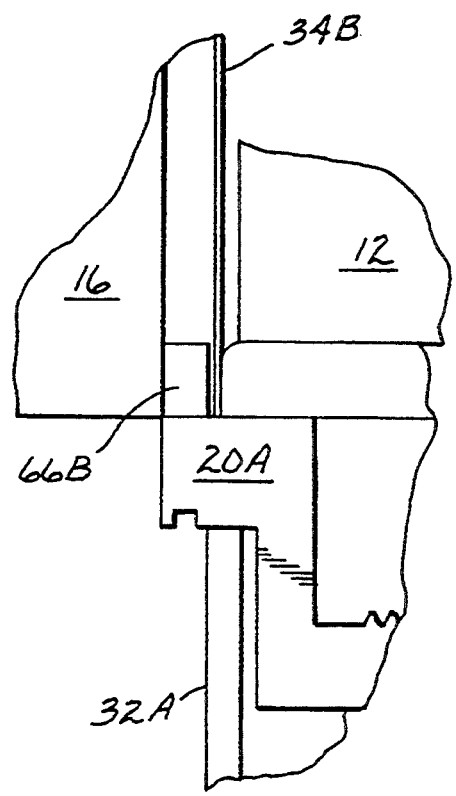
FIG. 8 is an enlarged diagrammatic view of selected portions of FIG. 7A and 7B illustrating various details of the mechanism for preventing mounting of more than one side module on one side of a center module.

As illustrated in FIG. 8, when the latching arms 20A of one module 12 are extended in their first position, they will engage a blocking member 66B on another module 16 if one attempts to mount another module on a "first" side module 12. The result is that the slide connections of the attempted "second" side module cannot be inserted into the slide connections of the "first" side module 12. In other word, more than one side module is prevented from being mounted on any one side of the center module 14. The arrangement is as illustrated in the drawing where at most two side modules 12 and 16 can be mounted on a center module 14, one side module 12 or 16 on each side of the center module 14. In such an arrangement, the securing means 44 of the center module 14 will have to support at most three modules 12, 14 and 16, and the maximum load will be balanced on opposite sides of the center module 14. The bottom surface 68A on continuous member 70A illustrated in FIG. 7A constitutes one alternative blocking means for engaging a latching arm to block connection of a "second" side module.

The latching arms 20, 20A, 20B, 22, 22A and 22B are mounted in the frame 18, 18A or 18B for sliding movement on pins 72 and 72A in FIGS. 3 and 4. Slots 74, 74A, 76 and 76A are provided in the latching arms 20, 20A, 20B, 22, 22A and 22B to receive the pins 72, 72A, and to allow movement of the latching arms 20, 20A, 20B, 22, 22A and 22B between their first and second positions.

One possible alternative means for moving the latching arms between their first and second conditions comprises an electrical switch arranged relative to the pole-securing bracket 46 to activate solenoid valves to withdraw the latching arms to their second condition. It is contemplated in that alternative that the solenoid valves would be of the pulse type. Other electromechanical means may also be employed to move the latching arms between their first and second positions.

Another alternative arrangement, which is not illustrated in the drawing, would be to provide downwardly-facing latching surfaces adjacent the lower ends of the slide connections, and upwardly-directed notches in the latching arms, which would also be positioned adjacent the lower end of the slide connection. In that alternative arrangement, the latching arms of a side module would be retracted in the first condition to allow the side module to be mounted on another (center) module in its second condition. The latching arms of the center module would be extended in the second condition to allow the downwardly-facing latching surface of the side module to interlock with the latching arms of the center module. In such an alternative, the latching arms would preferably be biased to their retracted position, and automatically extended to their extended position when the module is mounted on a pole stand.

The latching arms 20, 20A, 20B, 22, 22A and 22B may be considered as latching means for mounting the module 12, 14 or 16 on another module 12, 14 or 16, and the latching surfaces or shoulders 24, 24A, 24B, 26, 26A and 26B may be considered as latch-receiving means for allowing the latching means of another module 12, 14 or 16 to be mounted on the module 12, 14 or 16. One example of a condition-setting means is the tongue 64 which automatically moves the latching means (latching arms 20 and 22) to its second, non-latching position when the module 14 is mounted on the pole 17. In the second, non-latching position, the latching arms 20 and 22 are withdrawn into the module, with the result that the module 12 will allow other modules 14 or 16 to be mounted on its slide connections.

It is also contemplated that a detent (not shown) or positive locking means may be provided to prevent removal of a "side" module from a center module. For example, a detent could be provided on the slide connections, possibly by providing a spring-loaded ball detent in one of the slide connection (e.g., the female dovetail-type slide connections), and a detent-receiving recess in the other slide connection (e.g., the male dovetail-type slide connection) to increase resistance to lifting a side module from the center module. Another example would be to provide a manually operated latch (not shown) to positively lock a side module on the center module. In that arrangement, the side module could not be removed from the center module unless a button or lever was manually operated to release the latch. Such a latch might include a spring bias to its latched position such that the latch of the side module automatically clicks into a latch-receiving recess in the center module to lock them together.

Figure 9:
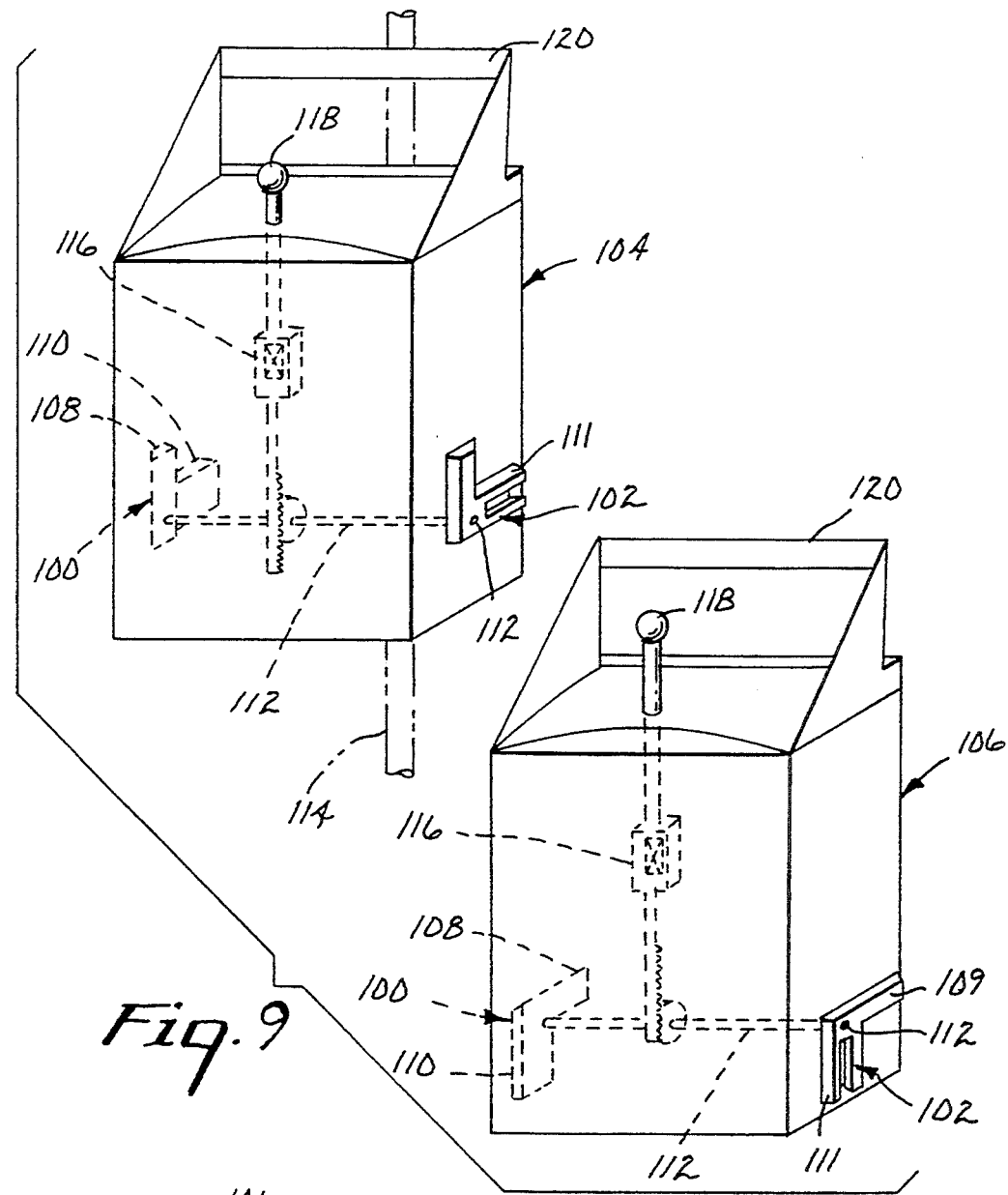
FIG. 9 is a frontal perspective view of two modules of an alternative embodiment of the invention.
Figure 10:
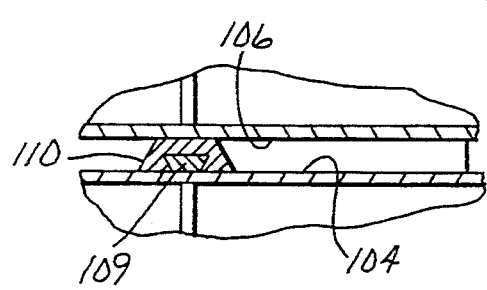
FIG. 10 is a cross-sectional view substantially along line 10—10 in FIG. 9 illustrating details of interlocking slide connections of that embodiment.
Figure 11:
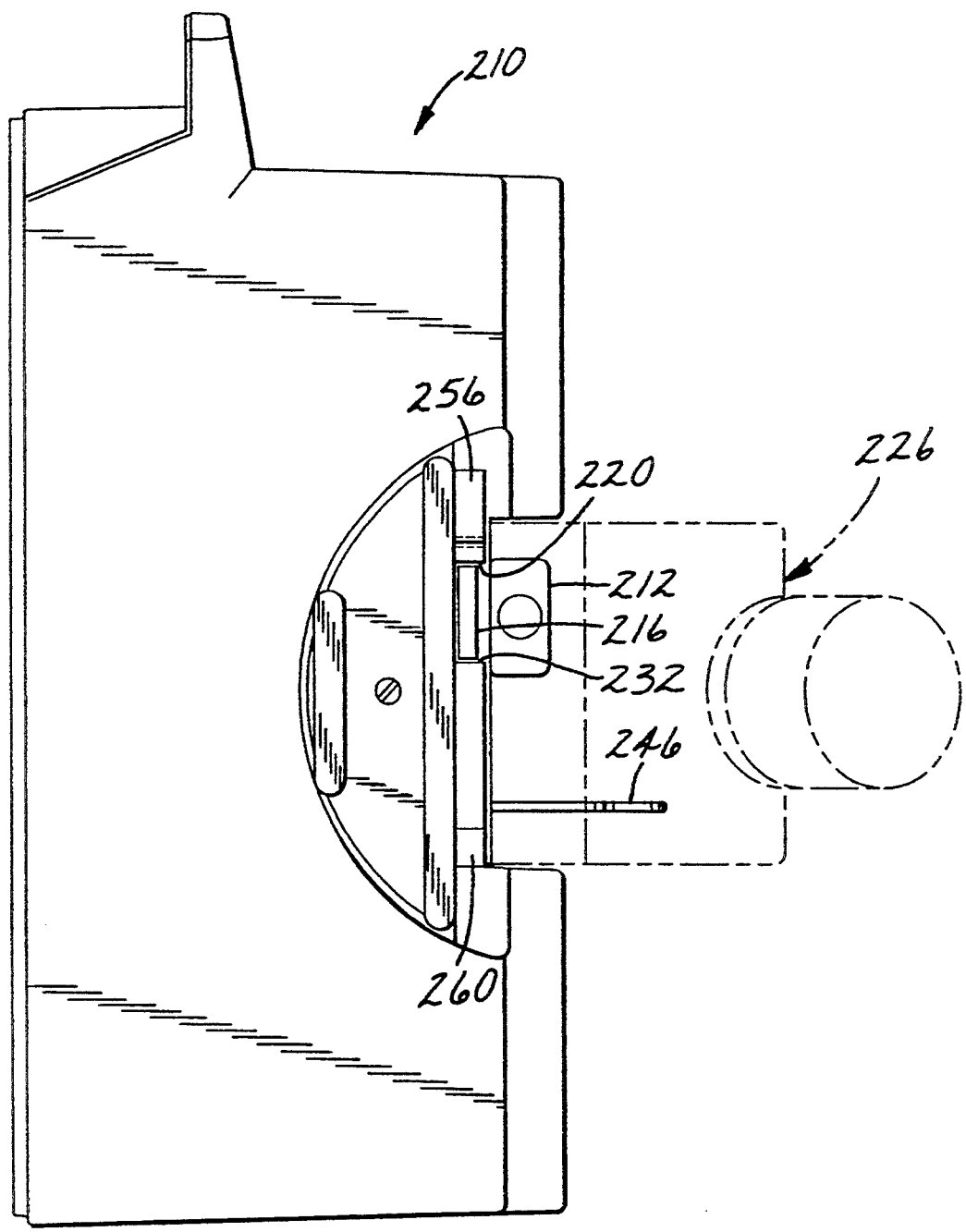
FIG. 11 is side view of a preferred embodiment of the medical device module of the invention, illustrating a novel interlocking mechanism.
Figure 12:
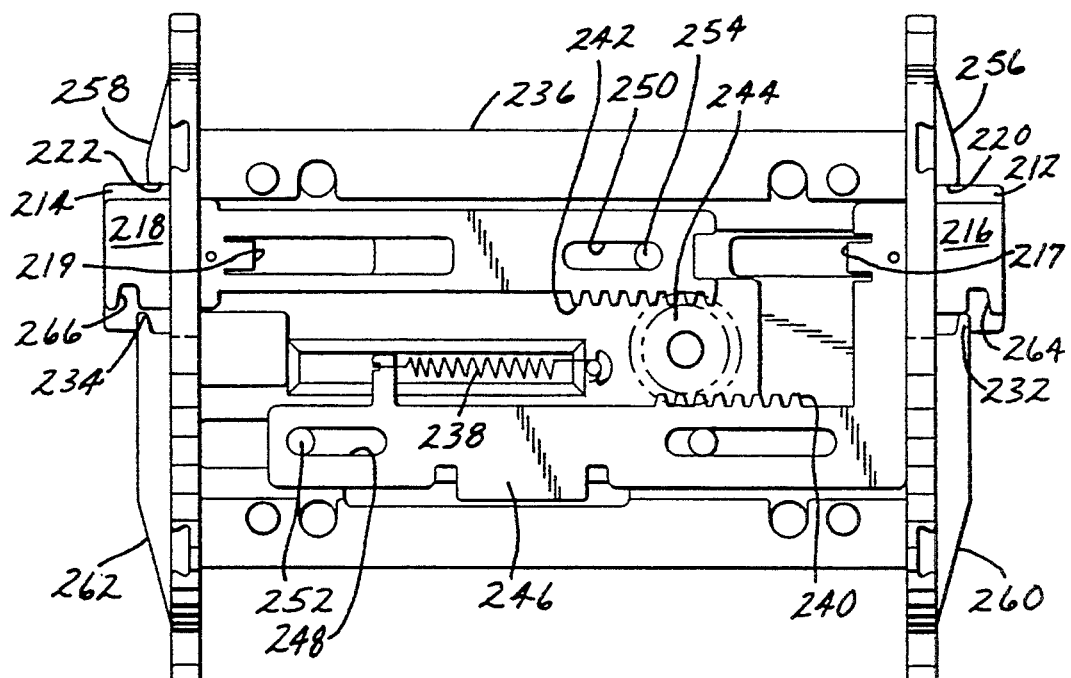
FIG. 12 is a front view of a portion of the interlocking mechanism of FIG. 11 illustrated separately from the medical device module, and showing the extended position of;the latching arms.

FIGS. 9 and 10 illustrate an alternative embodiment of the invention in which the interlocking means comprises a pair of generally L-shaped support bodies 100 and 102 rotatably mounted on opposite sides of the module 104 and 106. The same features on modules 104 and 106 are indicated by the same reference character. The modules 104 and 106 shown are "interchangeable" as defined above.

Each of the support bodies 100 and 102 has two legs 108 and 110 or 109 and 111. One leg 108, 109 comprises a male dovetail-type slide connection (also 108, 109) adapted for connection with a complementary female dovetail-type slide connection 110 or 111 of a similar module 106. The other leg 110, 111 comprising a female dovetail-type slide connection (also 110, 111) adapted for connection with a complementary male dovetail-type slide connection 108 or 109 of a similar module 104.

In the embodiment of FIGS. 9 and 10, the condition-setting means comprises means (e.g., axle 112 shown in phantom) for pivotably mounting the support bodies 100 and 102 on opposite sides of the module 104 and 106. The male dovetail-type slide connections 108 and 109 of the support bodies 102 and 104 are aligned in one direction (upwardly in module 104 and in the backward direction in module 106 in FIG. 9), and the female dovetail-type slide connections 110 and 111 of the support bodies 100 and 102 are aligned in another direction (backwardly in module 104 and downwardly in module 106 in FIG. 9) generally perpendicular to the direction of the male dovetail-type slide connections 108 and 109.

The support bodies 100 and 102 are pivotable between a first position (module 106 in FIG. 9) and a second position (module 104 in FIG. 9). In the first position, one aligned pair of the male or female dovetail-type slide connections 110 and 111 are aligned in the vertical direction. In the second position, the other aligned pair of said male or female dovetail-type slide connections 108 and 109 are aligned in the vertical direction.

The arrangement is such that the first position of the support bodies 100 and 102 corresponds to the first condition of the interlocking means, i.e., that the support bodies 100 and 102 of "side" module 106 are oriented to mount the module 106 on a "center" module 104 but the support bodies 100 and 102 "side" module 106 will not allow a second "side" module (not shown) to be mounted on the "side" module 106. The arrangement is also such that the second position of the support bodies 100 and 102 corresponds to the second condition of the interlocking means, i.e., that the support bodies 100 and 102 of "center" module 104 are oriented to allow a "side" module 106 to be mounted on the "center" module 104.

In the particular embodiment shown in FIG. 9, the male dovetail-type slide connections 108 and 109 must be aligned in the vertically upward direction ("center" module 104) to allow a "side" module 106 to be mounted thereon. The female dovetail-type slide connections 110 and 111 must be aligned in the vertically downward direction ("side" module 106) to be mounted on the male dovetail-type slide connections 108 or 109 of the "center" module 104. FIG. 10 is a cross-sectional illustration of a female dovetail-type slide connection 110 of module 106 mounted on a male dovetail-type slide connection 109 of module 104.

As was the case in the preferred embodiment, means (not shown) is provided for securing the module 104 or 106 on a pole 114. Biasing means generally indicated at 116 in phantom may be provided for biasing the support bodies 100 and 102 to one of their positions. The biasing means 116 shown in FIG. 9 can either be designed to bias the support bodies 100 and 102 to their first position (module 106) or to their second position (module 104).

The condition-setting means may comprise, in addition to an axle 112, manual or automatic means for setting the module 104 or 106 in its second condition upon securing the module 104 to a pole 114 via the securing means. Although automatic means of the general type described with respect to the embodiment of FIGS. 1-8 is preferred, manual means such as a pull-type knob 118 are shown in FIG. 9 for manually moving the support bodies 100 and 102 between their first and second positions. The pull-type knob 118 may include a handle (not shown) associated with the handle 120 of the module 104 or 106 to facilitate its operation.

FIGS. 11-15 illustrate a preferred embodiment of the module, here designated in its entirety by the reference numeral 210. Medical device module 210 is similar in some respects to the medical device module 10 illustrated in FIGS. 1-8, with two particularly notable exceptions being (1) the provision of push buttons 212 and 214 mounted on latching arms 216 and 218 for manually moving the latching arms 216 and 218 to their withdrawn position (FIGS. 13 and 15), and (2) the provision of upper shoulders 220 and 222 which are adapted to engage the upper side of the extended latching arm (not shown) of a similar module mounted on module 210 to prevent lifting that module off until its latching arms are manually moved to their withdrawn position.

Figure 15:
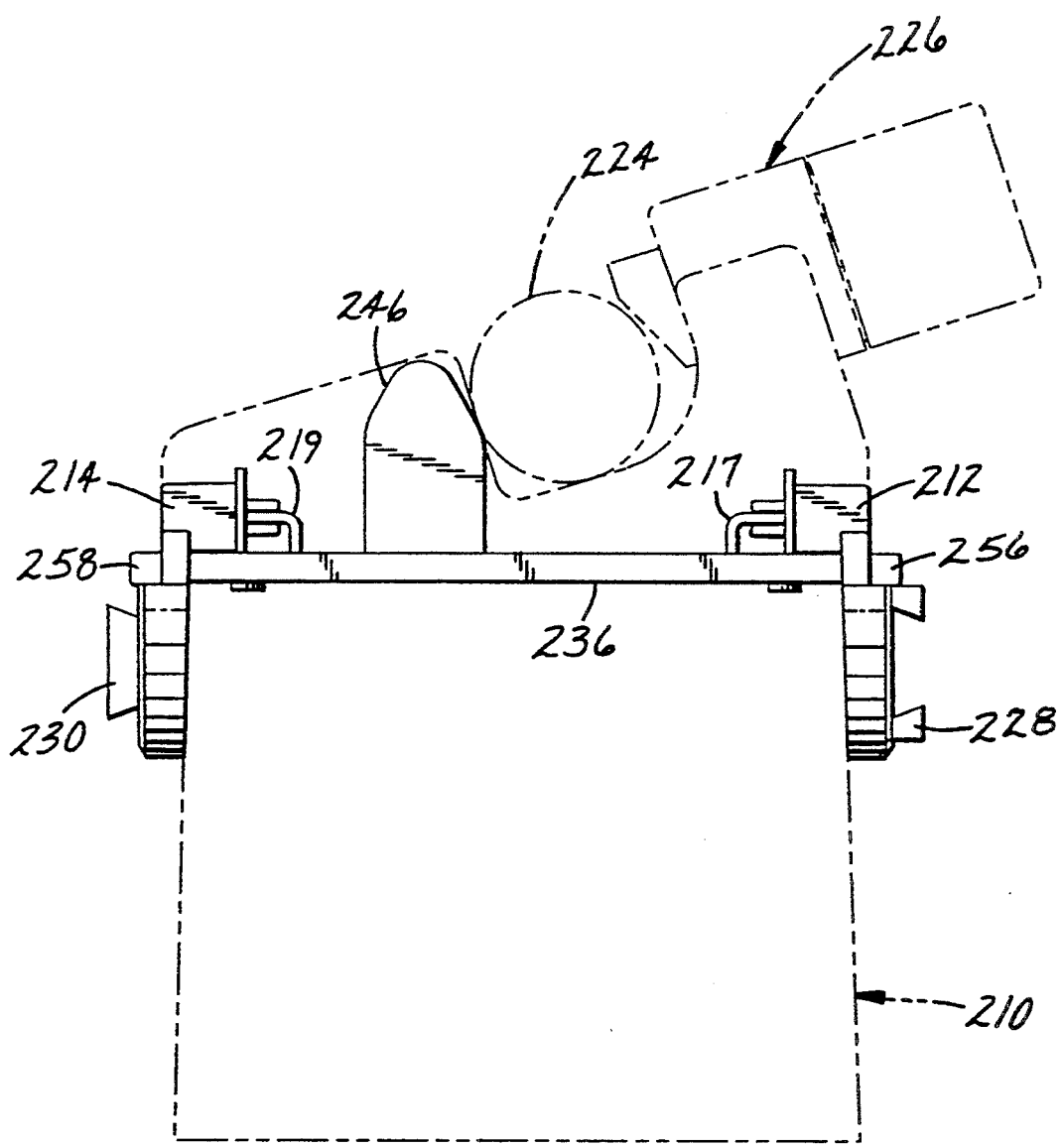
FIG. 15 is a top plan view similar to FIG. 14, illustrating the position of the tongue when after it is moved by a pole to move the latching arms to their withdrawn position.

More specifically, medical device module 210 is adapted for use in an interlocking system of similar modules (not shown) that are adapted to be mounted in side-by-side relationship on a pole stand (e.g., pole 224 shown in phantom in FIG. 15). The module 210 generally comprises suitable securing means generally designated 226 for securing the module 210 on a pole 224, and at least two slide connections 228 and 230 mounted on opposite sides of the module 210. The slide connection 228 on one side of the module 210 is complementary to the slide connection 230 on the other side of the module 210.

Two pairs of opposed latching shoulders are provided on the same opposite sides of the module 210 as the two slide connections 228 and 230. For example, upper latching shoulder 220 and lower latching shoulder 232, which are generally adjacent slide connection 228, constitute one pair of opposed latching shoulders 220 and 232 corresponding to slide connection 228. Upper latching shoulder 222 and lower latching shoulder 234, which are generally adjacent slide connection 230, constitute the second pair of opposed latching shoulders 222 and 234, which correspond to slide connection 230.

Figure 13:
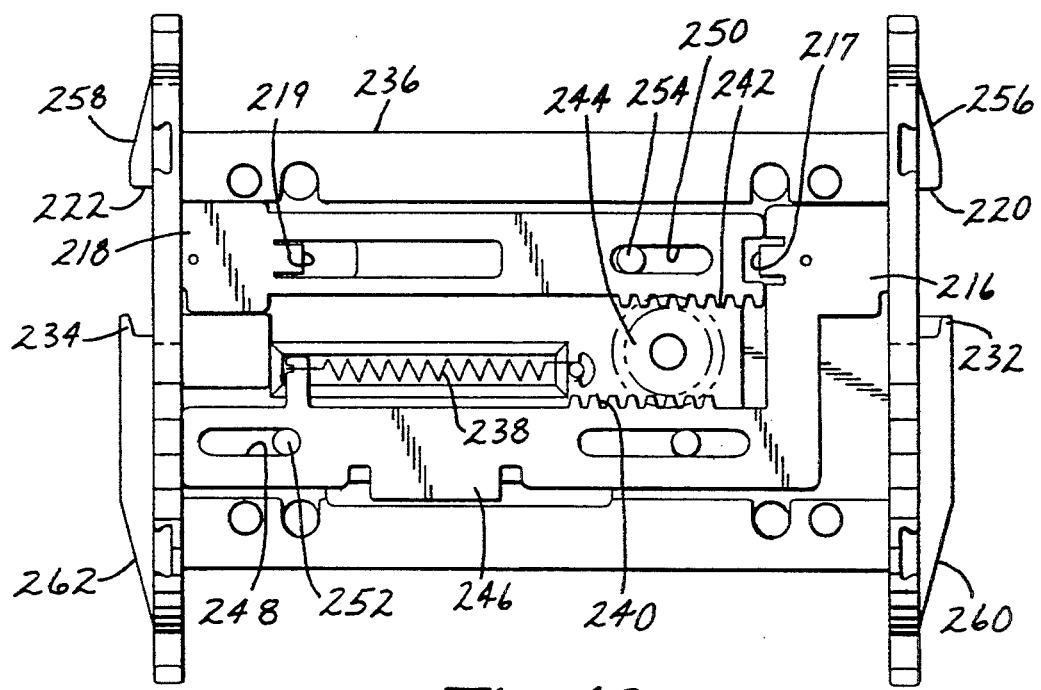
FIG. 13 is a front view similar to FIG. 12, showing the withdrawn position of the latching arms.
Figure 14:
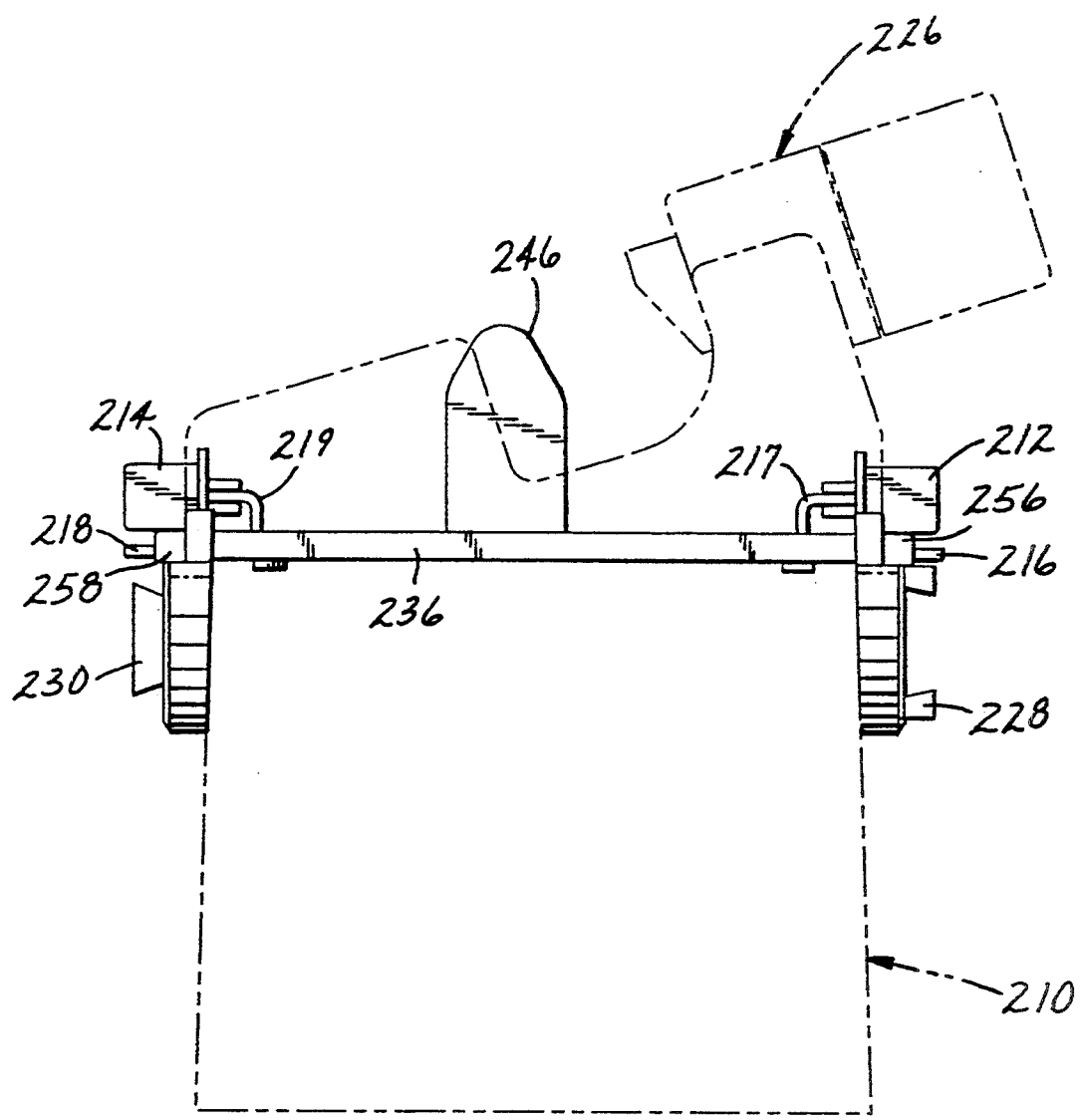
FIG. 14 is a top plan view of the interlocking mechanism of FIGS. 11–13, with other portions of the medical device module of FIG. 11 being shown in phantom, illustrating a tongue mounted on one of the latching arms when it extends into the pole-receiving means and the latching arms in their extended position.

Each latching arm 216 and 218 is mounted on the frame 236 of the module's interlocking mechanism for movement between an extended position (FIGS. 11, 12 and 14) and a withdrawn position (FIGS. 13 and 15).

In the extended position, both latching arms 216 and 218 extend a distance sufficient to (1) enable one of the latching arms 216 or 218 to be received between a pair of opposed latching shoulders of a similar module when the corresponding slide connection 228 or 230 are mounted on the slide connection of the similar module, thereby enabling the module 210 to be mounted on the similar module; and (2) enable the other of the latching arms 216 or 218 to block the other slide connection 228 or 230 from having a slide connection of a similar module mounted thereon. In other words, the module 210 can be mounted on another module (not shown) when its latching arms 216 and 218 are in their extended position, but no additional modules can be mounted on module 210 when the latching arms 216 and 218 are in their extended position. When the latching arms 216 and 218 are in their extended position, the interlocking mechanism is in its "side" module configuration.

When moved to their withdrawn position, the latching arms 216 and 218 are withdrawn relative to the slide connections 228 and 230 to allow a slide connection of a similar module to be mounted on either or both of the slide connections 228 and 230. When the latching arms 216 and 218 are in their withdrawn position, the interlocking mechanism is in its "center" module configuration.

Manually operable means, such as push buttons 212 and 214, is provided for moving the latching arms 216 and 218 from their extended position (FIGS. 11, 12 and 14) toward their withdrawn position (FIGS. 13 and 15) to permit moving either one of the latching arms 216 or 218 past the opposed latching shoulders of a similar module on which the module 210 is mounted to permit dismounting the module 210 from that similar module (not shown). The arrangement is such that pushing either push button 212 or 214 moves both latching arms 216 and 218 toward the withdrawn position. This allows the exposed push button 212 or 214 on one side of the module 210 to be manually pushed to move the latching arm 218 or 216 on the opposite side of the module 210 toward its withdrawn position to permit dismounting the slide connection 230 or 228 on opposite side from a slide connection (not shown) on which it was mounted. Each push button 212 and 214 is preferably mounted directly on, or integral with, its corresponding latching arm 216 or 218. For example, each latching arm 216 and 218 may be provided with a button-receiving tab 217 or 219 for mounting the respective push buttons 212 or 214.

Preferably, a suitable biasing means, such as spring 238 is provided for biasing the latching arms 216 and 218 to their extended position (e.g., FIG. 12), and automatic means is provided for moving the latching arms 216 and 218 against the bias of the biasing means 238 to their withdrawn position (e.g., FIG. 15) upon securing the module 210 to a pole 224 via the securing means 226.

The automatic means conveniently comprises a rack portion 240 and 242 having gear teeth (also 240 and 242) formed on each latching arm 216 and 218, a gear 244 rotatably mounted on the frame 236 of the interlocking mechanism of the module 210, and a tongue 246 on one of the latching arms 216 extending into the pole-receiving portion of the securing means 226. The gear teeth of the gear 244 are in intermeshing relationship with the gear teeth 240 and 242 of the latching arms 216 and 218 such that rotation of the gear 244 in one direction withdraws both latching arms 216 and 218 from their extended position (FIG. 12) to their withdrawn position (FIG. 13), and rotation of the gear 244 in the other direction extends both latching arms 216 and 218 from their withdrawn position to their extended position.

The tongue 246 extends into the pole-receiving portion of the securing means 226 such that when the tongue 246 is engaged by a pole 224 to which the securing means 226 is secured, the tongue 246 is moved by the pole 224 to move the latching arms 216 and 218 to their withdrawn position.

Most preferably, each latching arm 216 and 218 is provided with an elongate slot 248 or 250 that slidingly receives a pin 252 or 254 mounted on the frame 236 to prevent movement beyond the extended and withdrawn positions.

Also, preferably, the slide connections 228 and 230 comprise a female dovetail-type slide connection 228 on one side of the module 210, and a male dovetail-type slide connection 230 on the opposite side of the module 210, with the male dovetail-type slide connection 230 being complementary with the female dovetail-type slide connection 228. The slide connections 228 and 230 preferably have a direction of slide in the vertical direction, and the slide connections 228 and 230 have upper and lower ends relative to the intended use of the module 210.

Preferably, at least one latching shoulder 220 or 222 of each pair of latching shoulders is formed on a structure having a sloped surface 256 or 258 along the side of the structure facing away from the other latching shoulder 232 or 234. The sloped surface 256 or 258 is adapted to urge a latching arm of a similar module toward its withdrawn position against the biasing means of that module when the slide connection of the similar module is being mounted on the corresponding slide connection 228 or 230. When the latching arm of the similar module is positioned along the direction of slide between the pair of latching shoulders 220 and 232 or 222 and 234, the biasing means of the similar module biases the latching arm to its extended position so that the latching arm is securely received between the respective latching shoulders 220 and 232 or 222 and 234.

Preferably, the sloped surfaces 256 and 258 are provided along the upper shoulder-forming structure and face generally upwardly to facilitate mounting a "side" module on the "center" module 210 (FIGS. 13 and 15) by urging a latching arm of the "side" module toward its withdrawn position as the corresponding slide connection of the "side" module is slid downwardly along one of the slide connections 228 or 230 of the "center" module 210. Similar sloped surfaces 260 and 262 may be provided on the structures forming the lower latching shoulders 232 and 234. These additional surfaces 260 and 262 face generally downwardly to facilitate mounting a "side" module on a "center" module by urging the latching arms of the "side" module toward their withdrawn position as the "side" module is lifted relative to the "center" module.

Most preferably, the lower latching shoulders 232 and 234 extend outwardly relative to the module 210 slightly farther than the upper latching shoulders 220 and 222. This arrangement is believed to facilitate mounting a "side" module on the "center" module because the latching arm of the "side" module more readily catches such a lower latching shoulder 232 or 234 as a slide connection of the "side" module is lowered into one of the slide connections of the "center" module.

The lower latching shoulders 232 and 234 each preferably include a flange (also 232 or 234) extending generally vertically upwardly from the shoulder 232 or 234 along the outer edge of the shoulder 232 or 234. Each latching arm 216 and 218 has a downwardly-facing notch 264 or 266 generally adjacent the outer end of the latching arm 216 or 218, with the notches 264 and 266 of the latching arms 216 and 218 being complementary with the flanges 232 and 234 such that the notches 264 and 266 are adapted to receive the flanges (similar to flanges 232 and 234) of similar modules when the latching arms 216 and 218 are in their extended position.

The interlocking notch/flange arrangement prevents mounting a second "side" module on the side of a first "side" module. The notch/flange interlock between the flange 232 or 234 of the "center" module and the notch 264 or 266 of the "side" module would maintain the latching arms 216 and 218 of the "side" module in their extended position, and would not allow the latching arms 216 or 218 of the "side" module to retract as one of the latching arms 216 or 218 is engaged by the sloped end surface 256, 258, 260 or 262 of any attempted additional "side" module. The result is that the latching arms of the first "side" module are locked in their extended position, blocking mounting of additional "side" modules on the first "side" module.

The interlocking notch/flange arrangement also prevents a "side" module from being released from a "center" module by merely bumping one of the push buttons 212 or 214. To release a "side" module from the "center" module, the "side" module must be lifted slightly relative to the "center" module and the push button 212 or 214 must be pushed in.

It will be observed that the latching arm of the "side" module cannot be raised past the upper latching shoulder 220 or 222 unless the latching arm is moved toward its withdrawn position, and that the flange 260 or 262 of the "center" module will not allow the latching arm of the "side" module to be so withdrawn unless the "side" module is lifted slightly so that the notch of the latching arm clears the flange 260 or 262 of the "center" module. The distance between the upper end of the flange 260 and 262 and the upper latching shoulder 220 or 222 is preferably just slightly greater than height of the latching arm 216 or 218 to permit sufficient lifting of the "side" module from the "center" module to release the notch of the latching arm from the flange.

This arrangement is believed to help reduce the risk of accidentally releasing the latching arm of a "side" module from the latching shoulders of the "center" module.

The frame 236 of the interlocking mechanism of FIGS. 11–15 is particularly designed to be mounted along the back of the casing of the module 210. The low profile of the mid-portion of the frame 236 minimizes the space requirements of the interlocking mechanism. The interlocking mechanism is particularly designed to be used in medical device modules, such as infusion pumps.

OPERATION

The operation of the system 10 will be described with reference to the preferred embodiment shown in FIGS. 1–8. The center module 14 is first mounted on a pole stand 17 by clamping the pole 17 with the movable jaw 48. As the securing bracket 46 is brought around the pole 17, the tongue 64 is engaged by the pole 17 and moved out of the open space defined by the securing bracket 46, as illustrated in FIG. 2 by the relative position of the tongue 64 compared to either tongue 64A or 64B of the "side" modules.

The movement of the tongue 64 by the pole 17 causes the latching arms 20 and 22 to retract into the module 14. This is illustrated by the comparison of FIGS. 3 and 4. In FIG. 4, the tongue 64 has been engaged by the pole 17 to move latching arm 20 inwardly (rightwardly in FIG. 4), thus causing the gear 58 to rotate counterclockwise to move the other latching arm 22 inwardly (leftwardly in FIG. 4). The latching arms 20 and 22 are now withdrawn relative to the latching surfaces 24 and 26 and slide connections 32 and 34 to allow a slide connection of a similar module to be mounted on either/both slide connection 32 and 34. The center module 14 is now ready to have side modules 12 and/or 16 mounted thereon.

To mount the side modules 12 and/or 16 on the center module 14, the slide connections 32A, 32B, 34A or 34B of the side modules 12 or 16 are connected with the adjacent slide connection 32 or 34 of the center module 14 until the latching arm 22A or 20B engages the respective shoulder 24 or 26 of the center module 14. (The latching arms 20A, 20B, 22A and 22B of the "side" modules 12 and 16 are in their first position, in which they extend relative to the latching surfaces and slide connections of the respective side module 12 or 16 a distance sufficient to engage the shoulder 24 or 26 of a similar module 14 when one of the slide connections are mounted on the slide connection of the similar module 14.) At this point, the modules 12, 14 and 16 are properly interconnected on the pole 17.

Avoidance of Undesired Mounting Arrangements

Mounting of more than one module on one side of a center module 14 may be considered undesirable for a number of reasons, including the possibility of excessively unbalanced loads if two or three modules are mounted on one side of the center module and no modules are mounted on the other side. It may also be desired to limit the total number of modules to be mounted at one location on a pole 17 to prevent the pole-securing means 44 of the center module 14 from being overloaded.

Such undesired arrangements are prevented by the interengagement of the extended latching arms 20A and 22B of the side modules 16 and 12 with the blocking member 66B or blocking surface 68A of the undesired "second" side module. As illustrated in FIG. 8, if someone were to attempt to mount side module 16 on the right side 28A of a side module 12 that is already mounted on a center module 14, the extended latching arm 20A of the "first" side module 12 would engage the blocking member 66B to prevent the slide connections 32A and 34B from being interconnected. The use of the terms "first", "second" and "third", as used herein, may refer to any interchangeable module of the system. Whether a particular module is identified as being "first" "second" or "third" is arbitrary since the modules are interchangeable with respect to the claimed features. Depending upon context, the terms "first", "second" or "third" when applied to modules are analogous to "another", "other" or "yet another" module or modules of the system.

As various changes could be made in the above constructions without departing from the scope of the invention, it is intended that all matter contained in the above description or shown in the accompanying drawing be interpreted as illustrative and not in a limiting sense.

We claim:

1. A module adapted for use in an interlocking system of interchangeable modules designated herein as first or second interchangeable modules, said module comprising:
   a frame; and
   interlocking means on said frame for attaching at least two interchangeable modules having interlocking means to said module;
   said interlocking means including condition-setting means for setting said interlocking means in a first condition for mounting said module on an interchangeable module or a second condition for mounting the interchangeable module(s) thereon, such that:
   (a) when said interlocking means is set in its first condition (i) said interlocking means is capable of being mounted on the interlocking means of the first interchangeable module that has been set in its second condition, and (ii) said interlocking means of said module is not capable of having mounted thereon the interlocking means of the second interchangeable module; and
   (b) when said interlocking means is set in its second condition it is capable of having mounted thereon the interlocking means of at least two interchangeable modules that have been set in their first condition.

2. A module according to claim 1 further comprising securing means for securing said module to a pole.

3. A module according to claim 2 wherein said condition-setting means includes automatic means for setting said module in its second condition upon securing said module to the pole via said securing means.

4. A module according to claim 3 wherein said interlocking means comprises a male and a female dovetail-type slide connections, said male dovetail-type slide connection being complementary to said female dovetail-type slide connection, said male and female dovetail-type slide connections being arranged along the module such that the direction of slide in the connection is generally along a vertical axis.

5. A module according to claim 4 wherein said male and female dovetail-type slide connections are on opposite sides of said module, said male dovetail-type slide connection on one side of said module being complementary to said female dovetail-type slide connection on the other side of said module.

6. A module according to claim 4 wherein said condition-setting means further comprises:
   a shoulder adjacent each of said male and female dovetail-type slide connections; and
   shoulder-engaging means for engaging the shoulder on the first interchangeable module to enable said module to be mounted on the first interchangeable module when said condition-setting means is in its first condition and one of said male or female dovetail-type slide connections of said module is interconnected with the other of the male or female dovetail-type slide connections of the first interchangeable module;
   said shoulder-engaging means being movable, as said interlocking means is converted to its second condition from its first condition, to a position in which it does not engage the shoulder of the first or second interchangeable module.

7. A module according to claim 6 wherein said shoulder-engaging means comprises a pair of latching arms movable mounted on said frame for movement between a first position, corresponding to the first condition of said interlocking means, to a second position, corresponding to the second condition of said interlocking means;

the arrangement being such that, when said module has been set in its first condition, with said latching arms thus placed in their first position:

(a) one of said latching arms are adapted to engage a shoulder on the first interchangeable module, that has been placed in its second condition, when either one of said dovetail-type slide connection of said module is mounted on a complimentary dovetail-type slide connection on the first interchangeable module; and (b) said latching arms of said module are adapted to prevent such engagement of a dovetail-type slide connection of the second interchangeable module as would permit a latching arm of such second interchangeable module to engage either shoulder on said module.

8. A module according to claim 7 wherein said dovetail-type slide connections have upper and lower ends relative to the intended use of said module, each of said shoulders including a flange extending generally vertically upwardly from said shoulder along an outer edge of said shoulder, said shoulders being generally adjacent the upper ends of the dovetail-type slide connections; and each of said latching arms has a notch therein generally adjacent an outer end of said latching arm, the notches of said latching arms being adapted to receive the flanges of interchangeable modules when said latching arms are in their first position corresponding to the first condition of the interlocking means.

9. A module according to claim 7 wherein said shoulder-engaging means further comprises biasing means for biasing said latching arms to their first position, and arm-withdrawing means for withdrawing said latching arms from their first position to their second position, the arrangement of the first and second positions being such that said latching arms partially extend from said module when in their first position and are withdrawn into said module when in their second position.

10. A module according to claim 9 wherein said arm-withdrawing means comprises a gear rotatably mounted in said frame, and a rack of gear teeth on each of said latching arms, said latching arms being slidably mounted on said frame, with said gear teeth of said latching arms engaging said gear in a rack-and-pinion engagement.

11. A module according to claim 10 wherein said biasing means comprises a spring engaging said frame and one of said latching arms to bias said latching arms toward their first position.

12. A module according to claim 10 wherein the automatic means comprises a tongue operatively connected to at least one of said latching arms, said tongue being positioned, relative to said securing means, for engagement by the pole to move said tongue and latching arms to their second position.

13. A module according to claim 2 wherein said interlocking means comprises a male and a female dovetail-type slide connections on opposite sides of the module, said male dovetail-type slide connection being complementary to said female dovetail-type slid connection; and said condition-setting means further comprises:
a shoulder adjacent each of said male and female dovetail-type slide connections;
shoulder-engaging means for engaging one of the shoulders of the first interchangeable module to enable said module to be mounted on the first interchangeable module when said condition-setting means is in its first condition and one of said male or female dovetail-type slide connections of said module is interconnected with the other of the male or female dovetail-type slide connections of the first interchangeable module, said shoulder-engaging means being movable, as said interlocking means is converted to its second condition from its first condition, to a position in which it does not engage the shoulder of the first or second interchangeable module; and
manually operable means for moving said shoulder-engaging means between positions corresponding to the first and second conditions, said manually operable means comprising a knob rotatable mounted on the module and operatively connected to the shoulder engaging means.

14. A module according to claim 1 wherein said module is a medical instrument module.

15. A module according to claim 14 wherein said medical instrument module is an infusion pump.

16. A module according to claim 1 wherein said interlocking means comprises a pair of generally L-shaped support bodies rotatably mounted on opposite sides of said module, each of said support bodies having two legs including one leg comprising a male dovetail-type slide connection adapted for connection with a complementary female dovetail-type slide connection of the interchangeable modules, and another leg comprising a female dovetail-type slide connection adapted for connection with a complementary male dovetail-type slide connection of the interchangeable modules; said condition-setting means comprising:

means for pivotably mounting said support bodies on opposite sides of said module, with said male dovetail-type slide connections of said support bodies being aligned in one direction and said female dovetail-type slide connections of said support bodies being aligned in another direction generally perpendicular to the direction of said male dovetail-type slide connections;

said support bodies being pivotable between a first position, wherein one aligned pair of said male or female dovetail-type slide connections are aligned in the vertical direction, and a second position, wherein the other aligned pair of said male or female dovetail-type slide connections are aligned in the vertical direction.

17. A module according to claim 16 wherein the first position of said support bodies corresponds to the first condition of said interlocking means and the second position of said support bodies corresponds to the second condition of said interlocking means; said module further comprising:

means for securing said module on a pole; and
biasing means for biasing said support bodies to their first position;
said condition-setting means further comprising automatic means for setting said module in its second condition upon securing said module to the pole via the securing means.

18. A system for interlocking a plurality of interchangeable modules in side-by-side relationship, the system comprising a plurality of interchangeable modules including at least a first module, a second module, and a third module; each of the modules comprising:

a frame having opposite sides; and interlocking means on the frame adapted for attaching at least two other modules of the system to the module;

the interlocking means of the first module including condition-setting means for setting the interlocking means in a first condition for mounting the first module on a second module of the system or a second condition for mounting the second module and a third module of the system thereon, such that:

(a) when the interlocking means of the first module is set in its first condition (i) the interlocking means of the first module is capable of being mounted on the interlocking means of the second module of the system that has been set in its second condition, and (ii) the interlocking means of the first module is not capable of having mounted thereon the interlocking means of the third module of the system; and (b) when the interlocking means of the first module is set in its second condition it is capable of having mounted thereon the interlocking means of the second and third modules of the system that have been set in their first condition.

19. A system according to claim 18 wherein each of said modules further comprises securing means for securing the module to a pole.

20. A system according to claim 19 wherein the condition-setting means of each of said modules includes automatic means for setting the module in its second condition upon securing the module to the pole via the securing means.

21. A system according to claim 20 wherein the interlocking means of each of said modules comprises one of each of a male and a female dovetail-type slide connection, the male dovetail-type slide connection being complementary to the female dovetail-type slide connection of other modules of the system, the male and female dovetail-type slide connections being arranged along each of said modules such that the direction of slide in the connection is generally along a vertical axis.

22. A system according to claim 21 wherein the male and female dovetail-type slide connections are on opposite sides of each of said modules.

23. A system according to claim 21 wherein the condition-setting means of each of said modules further comprises:

a shoulder adjacent each of the male and female dovetail-type slide connections; and shoulder-engaging means for engaging one of the shoulders of the second module of the system to enable the first module to be mounted on the second module when the condition-setting means of the first module is in its first condition and one of the male or female dovetail-type slide connections of the first module is interconnected with the other of the male or female dovetail-type slide connections of the second module of the system;

the shoulder-engaging means of the first module being movable, as the interlocking means is converted to its second condition from its first condition, to a position in which it cannot engage the shoulder of the second or third module.

24. A system according to claim 23 wherein the shoulder-engaging means of each of said modules comprises a pair of latching arms movably mounted on the frame for movement between a first position, corresponding to the first condition of the interlocking means, to a second position, corresponding to the second condition of the interlocking means;

the arrangement being such that, when the interlocking means of the first module has been set in its first condition, with the latching arms of the first module thus placed in their first position:

(a) the latching arms of the first module are adapted to engage one of the shoulders of the second module, that has been placed in its second condition, when a dovetail-type slide connection of the first module is mounted on the complimentary dovetail-type slide connection on the second module; and (b) the latching arms of the first module are adapted to prevent the engagement of the dovetail-type slide connections of the third module as would permit a latching arm of said third module to engage either shoulder on the first module.

25. A system according to claim 24 wherein dovetail-type slide connections of each of said modules have upper and lower ends relative to the intended use of the module, each of said shoulders including a flange extending generally vertically upwardly from the shoulder along an outer edge of the shoulder, the shoulders being generally adjacent the upper ends of the dovetail-type slide connections; and each of said latching arms of the first module has a notch therein generally adjacent an outer end of the latching arm, the notches of the latching arms of the first module being adapted to receive a flange of the second module when the latching arms of the first module are in their first position corresponding to the first condition of the interlocking means.

26. A system according to claim 24 wherein the shoulder-engaging means of each of said modules further comprises biasing means for biasing the latching arms to their first position, and arm-withdrawing means for withdrawing the latching arms from their first position to their second position, the arrangement of the first and second positions being such that the latching arms of any module of the system partially extend from the module when in their first position and are withdrawn into the module when in their second position.

27. A system according to claim 26 wherein the arm-withdrawing means of each of said modules comprises a gear rotatably mounted in the frame, and a rack of gear teeth on each of the latching arms, the latching arms being slidably mounted on the frame, with the gear teeth of the latching arms engaging the gear in a rack-and-pinion engagement.

28. A system according to claim 27 wherein the biasing means of each of said modules comprises a spring engaging the frame and one of the latching arms to bias the latching arms toward their first position.

29. A system according to claim 27 wherein the automatic means of each of said modules comprises a tongue operatively connected to at least one of the latching arms, the tongue being positioned, relative to the securing means, for engagement by the pole to move the tongue and latching arms to their second position.

30. A system according to claim 19 wherein the interlocking means of each of said modules comprises a male and a female dovetail-type slide connection on opposite sides of the module, the male dovetail-type slide connection being complementary to the female dovetail-type slide connection; and the condition-setting means of each of said modules further comprises:

a shoulder adjacent each of the male and female dovetail-type slide connections;

shoulder-engaging means for engaging one of the shoulders of the second module to enable the first module to be mounted on the second module when the condition-setting means of the first module is in its first condition and one of the male or female dovetail-type slide connections of the first module is interconnected with the other of the male or female dovetail-type slide connections of the second module; the shoulder-engaging means of the first module being movable, as the interlocking means is converted to its second condition from its first condition, to a position in which the shoulder-engaging means of the first module cannot engage the shoulder of the second of third module; and manually operable means for moving the shoulder-engaging means between positions corresponding to the first and second conditions, the manually operable means comprising a knob rotatable mounted on each of the modules and operatively connected to the shoulder-engaging means.

31. A system according to claim 18 wherein the modules are medical instrument modules.

32. A system according to claim 31 wherein at least one medical instrument module is an infusion pump.

33. A system according to claim 18 wherein the interlocking means of each of said module comprises a pair of generally L-shaped support bodies rotatably mounted on opposite sides of the module, each of the support bodies having two legs including one leg comprising a male dovetail-type slide connection adapted for connection with a complementary female dovetail-type slide connection of the second module, and another leg comprising a female dovetail-type slide connection adapted for connection with a complementary male dovetail-type slide connection of the second module;

the condition-setting means of each of said modules comprising means for pivotably mounting the support bodies on opposite sides of the module, with the male dovetail-type slide connections of the module being aligned in one direction and the female dovetail-type slide connections of the module being aligned in another direction generally perpendicular to the direction of the male dovetail-type slide connections;

the support bodies of each of said modules being pivotable between a first position, wherein one aligned pair of the male or female dovetail-type slide connections are aligned in the vertical direction, and a second position, wherein the other aligned pair of the male or female dovetail-type slide connections are aligned in the vertical direction.

34. A system according to claim 33 wherein the first position of the support bodies corresponds to the first condition of the interlocking means and the second position of the support bodies corresponds to the second condition of the interlocking means; each of said modules further comprising:

means for securing the module on a pole; and biasing means for biasing the support bodies to their first position;

the condition-setting means further comprising automatic means for setting the module in its second condition upon securing the module to the pole via the securing means.

35. A medical instrument module adapted for use in an interlocking system of interchangeable modules, designated herein first and second interchangeable modules, that are adapted to be arranged in side-by-side relationship, said module comprising:

a frame having opposite sides;

securing means for securing said module to a pole; and interlocking means on said frame for attaching at least two interchangeable modules having interlocking means to said module;

said interlocking means including condition-setting means for setting said interlocking means in a first condition for mounting said module on the first interchangeable module or a second condition for mounting the first and second interchangeable module(e) thereon, such that:

(a) when said interlocking means is set in its first condition (i) said interlocking means is capable of being mounted on the interlocking means of the first interchangeable module that has been set in its second condition, and (ii) said interlocking means of said module is not capable of having mounted thereon the interlocking means of second interchangeable module; and (b) when said interlocking means is set in its second condition it is capable of having mounted thereon the interlocking means of the first and second interchangeable modules that have been set in their first condition.

36. A medical instrument module according to claim 35 wherein said condition-setting means includes automatic means for setting said module in its second condition upon securing said module to the pole via said securing means.

37. A medical instrument module according to claim 36 wherein said interlocking means comprises a male and a female dovetail-type slide connections on opposite sides of said module, said male dovetail-type slide connection being complementary to said female dovetail-type slide connection, said male and female dovetail-type slide connections being arranged along the module such that the direction of slide in the connection is generally along a vertical axis.

38. A medical instrument module according to claim 37 wherein said condition-setting means further comprises:

a shoulder adjacent each of said male and female dovetail-type slide connections; and shoulder-engaging means for engaging one of the shoulders of the first interchangeable module to enable said module to be mounted on the first interchangeable module when said condition-setting means is in its first condition and one of said male or female dovetail-type slide connections of said module is interconnected with the other of the male or female dovetail-type slide connections of the first interchangeable module;

said shoulder-engaging means being movable, as said interlocking means is converted to its second condition from its first condition, to a position in which it does not engage the shoulder of the first or the second interchangeable module.

39. A medical instrument module according to claim 38 wherein said shoulder-engaging means comprise a pair of latching arms movable mounted on said frame for movement between a first position, corresponding to the first condition of said interlocking means, to a second position, corresponding to the second condition of said interlocking means;

the arrangement being such that, when said module has been set in its first condition, with said latching arms thus placed in their first position:
(a) one of said latching arms is adapted to engage one of the shoulders of the first interchangeable module, that has been placed in its second condition, when either one of said dovetail-type slide connection of said module is mounted on a complimentary dovetail-type slide connection on the first interchangeable module; and
(b) said latching arms of said module are adapted to prevent the engagement of a dovetail-type slide connection of the second interchangeable module as would permit a latching arm of the second interchangeable module to engage either shoulder on said module.

40. A medical instrument module according to claim 39 wherein said dovetail-type slide connections have upper and lower ends relative to the intended use of said module, each of said shoulders including a flange extending generally vertically upwardly from said shoulder along an outer edge of said shoulder, said shoulders being generally adjacent the upper ends of the dovetail-type slide connections; and each of said latching arms has a notch therein generally adjacent an outer end of the latching arm, the notches of said latching arms being adapted to receive the flanges of interchangeable modules when said latching arms are in their first position corresponding to the first configuration of the interlocking means.

41. A medical instrument module according to claim 39 wherein said shoulder-engaging means further comprises biasing means for biasing said latching arms to their first position, and arm-withdrawing means for withdrawing said latching arms from their first position to their second position, the arrangement of the first and second positions being such that said latching arms partially extend from said module when in their first position and are withdrawn into said module when in their second position.

42. A medical instrument module according to claim 41 wherein said arm-withdrawing means comprises a gear rotatably mounted in said frame, and a rack of gear teeth on each of said latching arms, said latching arms being slidably mounted on said frame, with said gear teeth of said latching arms engaging said gear in a rack-and-pinion engagement.

43. A medical instrument module according to claim 42 wherein said biasing means comprises a spring engaging said frame and one of said latching arms to bias said latching arms toward their first position.

44. A medical instrument module according to claim 42 wherein the automatic means comprises a tongue operatively connected to at least one of said latching arms, said tongue being positioned, relative to said securing means, for engagement by the pole to move said tongue and latching arms to their second position.

45. A medical instrument module according to claim 36 wherein said interlocking means comprises a male and a female dovetail-type slide connection on opposite sides of the module, said male dovetail-type slide connection being complementary to said female dovetail-type slide connection; and said condition-setting means further comprises:
a shoulder adjacent each of said male and female dovetail-type slide connections;
shoulder-engaging means for engaging one of the shoulders of the first interchangeable module to enable said module to be mounted of the first interchangeable module when said condition-setting means is in its first condition and one of said male or female dovetail-type slide connections of said module is interconnected with the other of the male or female dovetail-type slide connections of the first interchangeable module, said shoulder-engaging means being movable, as said interlocking means is converted to its second condition from its first condition, to a position in which it does not engage the shoulder of the first or second interchangeable module; and
manually operable means for moving said shoulder-engaging means between positions corresponding to the first and second conditions, said manually operable means comprising a knob rotatable mounted on the module and operatively connected to the shoulder engaging means.

46. A medical instrument module according to claim 35 wherein said medical instrument module is an infusion pump.

47. A medical instrument module according to claim 46 wherein said condition-setting means includes automatic means for setting said interlocking means of said infusion pump in its second condition upon securing said infusion pump to the pole via said securing means.

48. A medical instrument module according to claim 47 wherein said interlocking means comprises a male and a female dovetail-type slide connection on opposite sides of said infusion pump, said male dovetail-type slide connection being complementary to said female dovetail-type slide connection, said male and female dovetail-type slide connections being arranged along said infusion pump such that the direction of slide in the connection is generally along a vertical axis.

49. A medical instrument module according to claim 48 wherein said condition-setting means further comprises:
a shoulder adjacent each of said male and female dovetail-type slide connections; and
shoulder-engaging means for engaging one of the shoulders of the first interchangeable module to enable said infusion pump to be mounted on the first interchangeable module when said condition-setting means is in its first condition and one of said male or female dovetail-type slide connections of said infusion pump is interconnected with the other of the male or female dovetail-type slide connections of the first interchangeable module;
said shoulder-engaging means being movable, as said interlocking means is converted to its second condition from its first condition, to a position in which it does not engage the shoulder of the first or second interchangeable module.

50. A medical instrument module according to claim 49 wherein said shoulder-engaging means comprises a pair of latching arms movable mounted on said frame for movement between a first position, corresponding to the first condition of said interlocking means, to a second position, corresponding to the second condition of said interlocking means;

the arrangement being such that, when said interlocking means of said infusion pump has been set in its first condition, with said latching arms thus placed in their first position:

(a) one of said latching arms is adapted to engage one of the shoulders of the first interchangeable module, that has been placed in its second condition, when either one of said dovetail-type slide connection of said infusion pump is mounted on the complimentary dovetail-type slide connection on the first interchangeable module; and (b) said latching arms of said infusion pump are adapted to prevent the engagement of a dovetail-type slide connection of the second interchangeable module as would permit a latching arm of the second interchangeable module to engage either shoulder on said infusion pump.

51. A medical instrument module according to claim 50 wherein said dovetail-type slide connections have upper and lower ends relative to the intended use of said infusion pump, each of said shoulders including a flange extending generally vertically upwardly from said shoulder along an outer edge of said shoulder, said shoulders being generally adjacent the upper ends of the dovetail-type slide connections; and each of said latching arms has a notch therein generally adjacent an outer end of the latching arm, the notches of said latching arms being adapted to receive the flanges of interchangeable modules when said latching arms are in their first position corresponding to the first configuration of the interlocking means.

52. A medical instrument module according to claim 50 wherein said shoulder-engaging means further comprises biasing means for biasing said latching arms to their first position, and arm-withdrawing means for withdrawing said latching arms from their first position to their second position, the arrangement of the first and second positions being such that said latching arms partially extend from said infusion pump when in their first position and are withdrawn into said infusion pump when in their second position.

53. A medical instrument module according to claim 52 wherein said arm-withdrawing means comprises a gear rotatably mounted in said frame, and a rack of gear teeth on each of said latching arms, said latching arms being slidably mounted on said frame, with said gear teeth of said latching arms engaging said gear in a rack-and-pinion engagement.

54. A medical instrument module according to claim 53 wherein said biasing means comprises a spring engaging said frame and one of said latching arms to bias said latching arms toward their first position.

55. A medical instrument module according to claim 53 wherein the automatic means comprises a tongue operatively connected to at least one of said latching arms, said tongue being positioned, relative to said securing means, for engagement by the pole to move said tongue and latching arms to their second position.

56. A medical instrument module according to claim 35 wherein said interlocking means comprises a pair of generally L-shaped support bodies rotatably mounted on opposite sides of said module, each of said support bodies having two legs including one leg comprising a male dovetail-type slide connection adapted for connection with a complementary female dovetail-type slide connection of the interchangeable module, and another leg comprising a female dovetail-type slide connection adapted for connection with a complementary male dovetail-type slide connection of the interchangeable module;

said condition-setting means comprising:

means for pivotably mounting said support bodies on opposite sides of said module, with said male dovetail-type slide connections of said support bodies being aligned in one direction and said female dovetail-type slide connections of said support bodies being aligned in another direction generally perpendicular to the direction of said male dovetail-type slide connections;

said support bodies being pivotable between a first position, wherein one aligned pair of said male or female dovetail-type slide connections are aligned in the vertical direction, and a second position, wherein the other aligned pair of said male or female dovetail-type slide connections are aligned in the vertical direction.

57. A medical instrument module according to claim 56 wherein the first position of said support bodies corresponds to the first condition of said interlocking means and the second position of said support bodies corresponds to the second condition of said interlocking means; said module further comprising:

means for securing said module on the pole; and biasing means for biasing said support bodies to their first position;

said condition-setting means further comprising automatic means for setting said module in its second condition upon securing said module to the pole via the securing means.

58. A medical instrument module adapted for use in an interlocking system of interchangeable medical instrument modules, herein designated first or second interchangeable modules, that are adapted to be mounted in side-by-side relationship on a pole stand, the module comprising:

a frame having opposite sides;

securing means for securing said module to a pole;

at least two slide connections mounted on opposite sides of said module, said slide connection on one side of the module being complementary to said slide connection on the other side of the module, said slide connections being arranged along the module such that the direction of slide in the connection is generally along a vertical axis when the module is in use;

at least two latching surfaces on the module, each corresponding to one of said slide connections, for engaging an arm of the second interchangeable module when said slide connection of said module is interconnected with a complimentary slide connection of the second interchangeable module; and a latching arm movably mounted in said frame for engaging a latching surface on the first interchangeable module to enable said module to be mounted on the first interchangeable module, said latching arm being movable between:

(a) a first position, (i) wherein said latching arm extends relative to said latching surfaces and slide connections a distance sufficient to engage the latching surface of the first interchangeable module when one of said slide connections are mounted on the slide connection of the first interchangeable module, and (ii) wherein said latching arm blocks said slide connection from having a slide connection of the second interchangeable module mounted thereon; and (b) a second position, wherein said latching arm is withdrawn relative to said latching surfaces and slide connections to allow a slide connection of the second interchangeable module to be mounted on said slide connection.

59. A medical instrument module according to claim 58 further comprising automatic means for moving said latching arm to its second position upon securing said module to the pole via said securing means.

60. A medical instrument module according to claim 58 wherein said latching arm comprises at least two latching arms at opposite sides of said module, each of said latching arms corresponding to one of said slide connections, each of said latching arms including a rack portion having gear teeth, said module further comprising a gear rotatably mounted on said frame and having gear teeth in intermeshing relationship with said gear teeth of said arms such that rotation of said gear in one direction withdraws said arms from the first position to their second position, biasing means for biasing said arms toward their first position, and a tongue on one of the arms extending into the securing means such that when said tongue is engaged by the pole to which the securing means is secured, said tongue is moved by the pole to move the arms to their second position.

61. A medical instrument module according to claim 60 wherein said slide connections comprise male and female dovetail-type slide connections on opposite sides of said module, said male and female dovetail-type slide connections being complementary to one another.

62. A medical instrument module according to claim 61 wherein said dovetail-type slide connections have upper and lower ends relative to the intended use of said module, each of said latching surfaces being formed by a shoulder including a flange extending generally vertically upwardly from said shoulder along an outer edge of said shoulder, said shoulders being generally adjacent said upper ends of said dovetail-type slide connections; and each of said latching arms has a notch therein generally adjacent an outer end of said latching arm, the notches of said latching arms being adapted to receive the flanges of the interchangeable modules when said latching arms are in their first position.

63. A medical instrument module according to claim 62 wherein said biasing means comprises a spring engaging said frame and one of said latching arms to bias said latching arms toward their first position.

64. A medical instrument module according to claim 58 wherein said medical instrument module is an infusion pump.

65. A medical instrument module according to claim 64 further comprising automatic means for moving said latching arm to its second position upon securing said infusion pump to the pole via said securing means.

66. A medical instrument module according to claim 65 wherein said latching arm comprises at least two latching arms at opposite sides of said infusion pump, each of said latching arms corresponding to one of said slide connections, each of said latching arms including a rack portion having gear teeth, said infusion pump further comprising a gear rotatably mounted on said frame and having gear teeth in intermeshing relationship with said gear teeth of said arms such that rotation of said gear in one direction withdraws said arms from the first position to their second position, biasing means for biasing said arms toward their first position, and a tongue on one of the arms extending into the securing means such that when said tongue is engaged by the pole to which the securing means is secured, said tongue is moved by the pole to move the arms to their second position.

67. A medical instrument module according to claim 66 wherein said slide connections comprise male and female dovetail-type slide connections on opposite sides of said module, said male and female dovetail-type slide connections being complementary to one another.

68. A medical instrument module according to claim 67 wherein said dovetail-type slide connections have upper and lower ends relative to the intended use of said module, each of said shoulders including a flange extending generally vertically upwardly from said shoulder along an outer edge of said shoulder, said shoulders being generally adjacent said upper ends of said dovetail-type slide connections; and each of said latching arms has a notch therein generally adjacent an outer end of said latching arm, the notches of said latching arms being adapted to receive the flanges of the interchangeable modules when said latching arms are in their first position.

69. A medical instrument module according to claim 68 wherein said biasing means comprises a spring engaging said frame and one of said latching arms to bias said latching arms toward their first position.

70. A medical device module adapted for use in an interlocking system of interchangeable medical device modules that are adapted to be mounted in side-by-side relationship on a pole stand, said module being referred to as a first module and the other modules of the system being referred to as second or third modules, the first module comprising:

securing means for securing said first module to a pole;

at least two slide connections mounted on opposite sides of said first module, said slide connection on one side of the first module being complementary to said slide connection on the other side of the first module;

two pairs of opposed latching shoulders on the same opposite sides of the first module as the two slide connections, each pair of opposed latching shoulders corresponding to one of said slide connections;

two latching arms, each latching arm being movably mounted in said first module for movement between:

an extended position, wherein said latching arms extend relative to said slide connections a distance sufficient to be received between a pair of opposed latching shoulders of the second module when one of said slide connections are mounted on the slide connection of the second module to enable said first module to be mounted on the second module, and wherein said latching arms block said slide connections from having a slide connection of the third module mounted thereon; and a withdrawn position, wherein said latching arms are withdrawn relative to said slide connections to allow a slide connection of the second module to be mounted on said slide connections; and manually operable means for moving said latching arms from their extended position toward their withdrawn position to permit moving one of said latching arms past the opposed latching shoulders of the second module on which said first module is mounted to permit dismounting said first module from the second module.

71. A medical device module according to claim 70 wherein the manually operable means comprises a push button mounted on each said latching arm to facilitate manually pushing the latching arms from their extended position toward their withdrawn positions.

72. A medical device module according to claim 71 wherein one of the latching shoulders of each said pair of opposed latching shoulders is formed on a structure having a sloped surface along the side facing away from the other latching shoulder to urge a latching arm of the second module toward its withdrawn position when the slide connection of the second module is being slidably mounted on said slide connection of said first module until the latching arm of the second module is received between said pair of opposed latching shoulders; the first module further comprising biasing means for biasing the latching arms toward their extended position.

73. A medical device module according to claim 72 further comprising automatic means for moving said latching arms against the biasing force of the biasing means to the withdrawn position upon securing said first module to the pole via said securing means.

74. A medical device module according to claim 73 wherein the slide connections have a direction of slide in the vertical direction, the sloped surface facing generally upwardly.

75. A medical device module according to claim 74 wherein said automatic means comprises:
a rack portion having gear teeth on each said latching arm;
a gear rotatably mounted in said module and having gear teeth in intermeshing relationship with said gear teeth of said latching arms such that rotation of said gear in one direction withdraws said latching arms from their extended position to their withdrawn position; and
a tongue on one of said latching arms extending into the securing means such that when said tongue is engaged by a pole to which said securing means is secured, said tongue is moved by the pole to move said latching arms to their withdrawn position.

76. A medical device module according to claim 74 wherein:
said slide connections comprise male and female dovetail-type slide connections on opposite sides of said first module, said male and female dovetail-type slide connections being complementary to one another, said dovetail-type slide connections having upper and lower ends relative to the intended use of said first module;
each said pair of opposed latching shoulders including an upper latching shoulder and a lower latching shoulder, the lower latching shoulder including a flange extending generally vertically upwardly from said shoulder along an outer edge of said shoulder, said shoulders being generally adjacent said upper ends of said dovetail-type slide connections;
each said latching arm having a downwardly-facing notch therein generally adjacent an outer end of said latching arm, the notches of said latching arms of the first module being adapted to receive the flanges of the second module when said latching arms of the first module are in their extended position.

77. A medical device module according to claim 70 wherein said first module is an infusion pump.

78. An interlocking module system comprising at least two interchangeable medical device modules that are adapted to be mounted in side-by-side relationship on a pole stand, each module comprising:
securing means for securing said module to a pole;
at least two slide connections mounted on opposite sides of said module, said slide connection on one side of the module being complementary to said slide connection on the other side of the module;
two pair of opposed latching shoulders on the same opposite sides of the module as the two slide connections, each pair of opposed latching shoulders corresponding to one of said slide connections;
two latching arms, each latching arm being movably mounted in said module, herein constituting a first module, for movement between:
an extended position, wherein said latching arms extend relative to said slide connections a distance sufficient to be received between a pair of opposed latching shoulders of a second module of the system when one of said slide connections are mounted on the slide connection of the second module to enable said first module to be mounted on the second module, and wherein said latching arms block said slide connections from having a slide connection of a third module of the system mounted thereon; and
a withdrawn position, wherein said latching arms are withdrawn relative to said slide connections to allow a slide connection of the second module of the system to be mounted on said slide connections; and
manually operable means for moving said latching arms from their extended position toward their withdrawn position to permit moving one of said latching arms past the opposed latching shoulders of said second module of the system on which said first module is mounted to permit dismounting said first module from the second module.

79. A system according to claim 78 wherein the manually operable means comprises a push button mounted on each said latching arm to facilitate manually pushing the latching arms from their extended position toward their withdrawn positions.

80. A system according to claim 79 wherein one of the latching shoulders of each said pair of opposed latching shoulders is formed on a structure having a sloped surface along the side facing away from the other latching shoulder to urge a latching arm of said second module of the system toward its withdrawn position when the slide connection of the second module is being slidably mounted on said slide connection of said first module until the latching arm of the second module is received between said pair of opposed latching shoulders; each said module further comprising biasing means for biasing the latching arms toward their extended position.

81. A system according to claim 80 further comprising automatic means for moving said latching arms against the biasing force of the biasing means to the withdrawn position upon securing said module to the pole via said securing means.

82. A system according to claim 81 wherein the slide connections have a direction of slide in the vertical direction, the sloped surface facing generally upwardly.

83. A system according to claim 82 wherein said automatic means comprises:
   a rack portion having gear teeth on each said latching arm;
   a gear rotatably mounted in said module and having gear teeth in intermeshing relationship with said gear teeth of the rack portions of said latching arms such that rotation of said gear in one direction withdraws said latching arms from their extended position to their withdrawn position; and
   a tongue on one of said latching arms extending into the securing means such that when said tongue is engaged by a pole to which said securing means is secured, said tongue is moved by the pole to move said latching arms to their withdrawn position.

84. A system according to claim 82 wherein:
   said slide connections comprise male and female dovetail-type slide connections on opposite sides of said module, said male and female dovetail-type slide connections being complementary to one another, said dovetail-type slide connections having upper and lower ends relative to the intended use of said module;
   each said pair of opposed latching shoulders including an upper latching shoulder and a lower latching shoulder, the lower latching shoulder including a flange extending generally vertically upwardly from said shoulder along an outer edge of said shoulder, said shoulders being generally adjacent said upper ends of said dovetail-type slide connections;
   each said latching arm having a downwardly-facing notch therein generally adjacent an outer end of said latching arm, the notches of said latching arms of the first module of the system being adapted to receive the flanges of the second module of the system when said latching arms of the first module are in their extended position.

85. A system according to claim 78 wherein at least one of said medical device modules is an infusion pump.

* * * * *